US012108804B2

(12) United States Patent
Woodbine et al.

(10) Patent No.: US 12,108,804 B2
(45) Date of Patent: Oct. 8, 2024

(54) SMART VAPORIZER AND SYSTEM FOR CONCENTRATE PRODUCTS

(71) Applicant: GoFire, Inc., Denver, CO (US)

(72) Inventors: John Jesse Woodbine, Lafayette, CO (US); Peter William Calfee, Dorset, VT (US); Gary Ross Mitchell, Lyons, CO (US); William F Demyanovich, Lyons, CO (US); Joseph Freancis Keenan, Superior, CO (US)

(*) Notice: Subject to any disclaimer, the term of this patent is extended or adjusted under 35 U.S.C. 154(b) by 943 days.

(21) Appl. No.: 17/047,204

(22) PCT Filed: Apr. 22, 2019

(86) PCT No.: PCT/US2019/028541
§ 371 (c)(1),
(2) Date: Oct. 13, 2020

(87) PCT Pub. No.: WO2019/204812
PCT Pub. Date: Oct. 24, 2019

(65) Prior Publication Data
US 2021/0161213 A1 Jun. 3, 2021

Related U.S. Application Data

(60) Provisional application No. 62/660,974, filed on Apr. 21, 2018.

(51) Int. Cl.
*A24F 40/53* (2020.01)
*A24F 7/02* (2006.01)
(Continued)

(52) U.S. Cl.
CPC ............... *A24F 40/53* (2020.01); *A24F 7/02* (2013.01); *A24F 40/10* (2020.01); *A24F 40/20* (2020.01);
(Continued)

(58) Field of Classification Search
CPC .......... A24F 40/53; A24F 40/65; A24F 40/48; A24F 40/10; A24F 40/46; A24F 40/20;
(Continued)

(56) References Cited

U.S. PATENT DOCUMENTS 4,934,358 A 6/1990 Nilsson et al.
4,947,875 A 8/1990 Brooks et al.
(Continued)

FOREIGN PATENT DOCUMENTS

EP 2399636 12/2011
EP 2207528 10/2013
(Continued)

OTHER PUBLICATIONS

PCT International Search Report for International Application PCT/US2019/028541, search report dated Aug. 30, 2019 (dated Aug. 30, 2019).

*Primary Examiner* — Peter G Leigh
(74) *Attorney, Agent, or Firm* — Daniel W. Roberts; Law Offices of Daniel W. Roberts, LLC

(57) ABSTRACT

An improved vaporizer, system, and method for managing concentrate usage is disclosed. The vaporizer may comprise a housing to receive a cartridge configured to store a concentrate. The cartridge comprises a nozzle, at one end, with a smart chip for storing an identification code associated with the concentrate. The vaporizer, cartridge, system and method provides means for assuring accurate dosing and management of concentrate use and usage data collection.

39 Claims, 14 Drawing Sheets

(51) Int. Cl.
*A24F 40/10* (2020.01)
*A24F 40/20* (2020.01)
*A24F 40/42* (2020.01)
*A24F 40/46* (2020.01)
*A24F 40/48* (2020.01)
*A24F 40/51* (2020.01)
*A24F 40/57* (2020.01)
*A24F 40/60* (2020.01)
*A24F 40/65* (2020.01)
*A61M 15/06* (2006.01)

(52) U.S. Cl.
CPC .............. *A24F 40/42* (2020.01); *A24F 40/46* (2020.01); *A24F 40/48* (2020.01); *A24F 40/51* (2020.01); *A24F 40/57* (2020.01); *A24F 40/60* (2020.01); *A24F 40/65* (2020.01); *A61M 15/06* (2013.01)

(58) Field of Classification Search
CPC .......... A24F 40/57; A24F 40/42; A24F 40/51; A24F 40/60; A24F 7/02
USPC ......................................................... 131/328
See application file for complete search history.

(56) References Cited

U.S. PATENT DOCUMENTS

| | | |
|---|---|---|
| 5,284,133 A | 2/1994 | Burns et al. |
| 5,950,619 A | 9/1999 | Kubdeb et al. |
| 6,772,756 B2 | 8/2004 | Shayan |
| 6,814,083 B2 | 11/2004 | Likness et al. |
| 7,088,914 B2 | 8/2006 | Whittle et al. |
| 7,164,993 B2 | 1/2007 | Likness et al. |
| 7,540,286 B2 | 6/2009 | Cross et al. |
| 8,464,706 B2 | 6/2013 | Crockford et al. |
| 8,550,069 B2 | 10/2013 | Alelov |
| 8,602,037 B2 | 12/2013 | Inagaki |
| 8,851,068 B2 | 10/2014 | Cohen et al. |
| 8,897,628 B2 | 11/2014 | Conley et al. |
| 8,899,239 B2 | 12/2014 | Hon |
| 8,910,630 B2 | 12/2014 | Todd |
| 9,220,294 B2 | 12/2015 | McCullough |
| 9,320,301 B2 | 4/2016 | Memari et al. |
| 9,380,813 B2 | 7/2016 | McCullough |
| 9,462,832 B2 | 10/2016 | Lord |
| 2013/0340775 A1 | 12/2013 | Juster et al. |
| 2014/0116455 A1 | 5/2014 | Youn |
| 2014/0202477 A1 | 7/2014 | Qi et al. |
| 2014/0243749 A1 | 8/2014 | Edwards et al. |
| 2014/0278250 A1 | 9/2014 | Smith et al. |
| 2014/0345633 A1 | 11/2014 | Talon et al. |
| 2014/0345635 A1 | 11/2014 | Rabinowitz et al. |
| 2015/0039591 A1 | 2/2015 | Ding et al. |
| 2015/0053217 A1 | 2/2015 | Steingraber et al. |
| 2015/0136158 A1 | 5/2015 | Stevens et al. |
| 2015/0142387 A1 | 5/2015 | Alarcon et al. |
| 2015/0181945 A1 | 7/2015 | Tremblay |
| 2015/0245660 A1 | 9/2015 | Lord |
| 2015/0272220 A1 | 10/2015 | Spinka et al. |
| 2015/0320116 A1 | 11/2015 | Bleloch et al. |
| 2015/0327596 A1 | 11/2015 | Alarcon et al. |
| 2015/0332379 A1 | 11/2015 | Alarcon |
| 2015/0366266 A1 | 12/2015 | Shabat |
| 2016/0007651 A1 | 1/2016 | Ampolini et al. |
| 2016/0021930 A1 | 1/2016 | Minskoff et al. |
| 2016/0089508 A1 | 3/2016 | Smith et al. |
| 2016/0106936 A1 | 4/2016 | Kimmel |
| 2016/0143361 A1 | 5/2016 | Juster et al. |
| 2016/0157524 A1 | 6/2016 | Bowen et al. |
| 2016/0200463 A1 | 7/2016 | Hodges et al. |
| 2016/0211693 A1* | 7/2016 | Stevens ................ H04W 48/16 |
| 2016/0219932 A1 | 8/2016 | Glaser |
| 2016/0219933 A1 | 8/2016 | Henry, Jr. et al. |
| 2016/0219938 A1 | 8/2016 | Mamoun et al. |
| 2016/0278435 A1 | 9/2016 | Choukroun et al. |
| 2016/0309784 A1 | 10/2016 | Silvestrini et al. |
| 2016/0309789 A1 | 10/2016 | Thomas, Jr. |
| 2016/0331027 A1 | 11/2016 | Cameron |
| 2016/0331913 A1 | 11/2016 | Bourque |
| 2016/0337141 A1 | 11/2016 | Cameron |
| 2016/0356751 A1 | 12/2016 | Blackley |
| 2016/0363570 A1 | 12/2016 | Blackley |
| 2016/0363917 A1 | 12/2016 | Blackley |
| 2017/0046357 A1 | 2/2017 | Cameron |
| 2017/0265524 A1* | 9/2017 | Cadieux ................ H05B 3/42 |
| 2018/0043114 A1* | 2/2018 | Bowen ................ A24F 40/60 |
| 2018/0177958 A1 | 6/2018 | Wilder et al. |

FOREIGN PATENT DOCUMENTS

| | | |
|---|---|---|
| EP | 3099363 | 12/2016 |
| EP | 3102266 | 12/2016 |
| GB | 2524779 | 10/2015 |
| KR | 2015065072 | 6/2015 |
| WO | WO03097141 | 11/2003 |
| WO | WO2016009202 | 1/2016 |
| WO | WO2016050247 | 4/2016 |
| WO | WO2016064906 | 4/2016 |
| WO | WO2016172802 | 11/2016 |
| WO | WO2016187695 | 12/2016 |

\* cited by examiner

1100

SMART VAPORIZER AND SYSTEM FOR CONCENTRATE PRODUCTS

CROSS-REFERENCE TO RELATED APPLICATIONS

This application discloses a number of improvements over and enhancements to the concentrate vaporizers and systems disclosed in the inventor's U.S. patent application Ser. Nos. 15/391,829 and 62/721,699 which are incorporated herein by their reference.

FIELD OF THE DISCLOSURE

The present invention relates to an improved vaporizer, system and method for managing and optimizing concentrate's vapor quality, vaporizer's efficiency, and user experience.

BACKGROUND TO THE DISCLOSURE

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Vaporizing devices are readily known and used for medical and recreational reasons. Existing vaporizing devices allow users to operate by loading a desired quantity of a concentrate product (optionally pre-packaged in a cartridge unit), into a vaporization chamber of the device. Generally, the mechanisms for loading the concentrate are complex to operate, and as a result, the user may end up consuming erratic quantity of the concentrate in some vaping sessions. Furthermore, the user is typically unaware of the concentrate being used owing to lack of availability of information related to the concentrate. Vaporizing devices such as Pax 3™ and Firefly 2™ do not have a cartridge based system, and therefore, relies on the concentrate product's primary package labeling as a means of suggesting the concentrate dosage delivered to a user.

Numerous methods of loading a cartridge into a vaporizer exist. However, these methods can be cumbersome and present usability problems such as ineffective cartridge sealing and cleaning capabilities. Many existing vaporizers are not capable of cleanly and accurately dosing concentrates or concentrate essential oils for inhalation. Vaporizers, such as the Pax 3™, require manual fill whereby a user must use precision tools, such as metered syringes, to achieve accurately controlled dosing. These tools are difficult to source and contribute additional cost to the vaporizer. In the case of vaporizers for medical use, such limitations do not allow users and physicians to confidently and consistently administer and/or prescribe concentrate dose regimens best suited for their needs. Some concentrate vaporization devices have addressed dosing issues by utilizing the inhaled flow rate as a means to control dosing. However, such devices fail to adequately provide uniform vaporization of the concentrates, resulting in a mismatch between prescribed/desired dosage and actual amounts received by the user.

Further, there is a lack of technology that allows for dosing of different types of materials (i.e., products) intended for use in vaporization devices. These materials can be, for instance, granular, powdered, loose leaf, flower, aromatic, medicinal, waxy, paste, thick oil, or other physical materials capable of being portioned and delivered (such as by use of an auger mechanism) through a vaporizer device. Likewise, most raw materials intended for vaporization vary in consistency and have not been standardized in a way that can be portioned into uniform doses. Dosing of such products is also compromised in that they are often loaded by hand. What is needed is an "all-in-one" vaporizer that allows controlled uniform dosing and tracking of the chemical compounds of the products contained inside the cartridge regardless of the product's physical form and/or constituents.

U.S. patent application Ser. No. 15/924,172 discloses a method and apparatus for cloud integration control of medicine delivery parameters in an electronic vaporizer. Also, U.S. patent application Ser. No. 12/780,876 discloses a data logging personal vaporizing inhaler. Further, U.S. patent application Ser. No. 13/840,588 discloses an inhaler controlled by mobile device.

In view of existing vaporizers, there is a need to maintain the operational certainty of vaporizers as it relates to vapor sealing, dose integrity, and corresponding direct user feedback at a minimum. In addition, existing vaporizers do not provide a feedback system to alert a user that concentrate product has been completely vaporized or that a concentrate dosing session has been properly completed. Therefore, there is a need of a concentrate product vaporizer which enables the user to administer the concentrate in desired dosages, and further manages, logs, tracks and/or monitors the concentrate usage of the user, and provides improved operational efficiencies.

BRIEF DESCRIPTION OF THE EMBODIMENTS

In one aspect, a system for managing concentrate usage is disclosed. The system may comprise a vaporizer, a user device, and a central server. The vaporizer may comprise a housing, wherein the housing may comprise a cartridge configured to store a concentrate. The cartridge may comprise a nozzle, at one end, with a smart chip containing an identification code associated with the concentrate and a dosing mechanism at another end. The housing of the vaporizer may also comprise a control unit configured to read the identification code from the smart chip on the nozzle and control operation of an oven. The oven may be adjacent to the nozzle of the cartridge. A communication unit may be coupled to the control unit, wherein the communication unit may transmit the identification code to the user device. The system may also comprise the central server having a database for storing a plurality of identification codes against a plurality of concentrate information. The central server may be configured to receive the identification code from the user device. The central server may retrieve concentrate information corresponding to the received identification code from the database. The central server may transmit the retrieved concentrate information to the user device.

In an embodiment, the dosing mechanism may be adjacent to a mouthpiece of the vaporizer. The dosing mechanism may comprise a plunger driver, a pawl, and a plunger. Upon rotation of a dosing wheel by a user, the plunger driver may drive the plunger within the cartridge to release a predefined quantity of the concentrate through the nozzle.

The oven may comprise a coil placed within a thermally resistant tube, an airflow channel in communication with ambient air and inhalation negative pressure airflow, and a dose diffuser containing a porous material matrix or screen (e.g., a gold-plated metal mesh). The control unit may be configured to heat the coil of the oven based on at least one of a fire button, an in-line pressure sensor, a fan/IR reflector sensor, and the identification code associated with the concentrate. The control unit may heat the coil to vaporize the predefined quantity of the concentrate released through the nozzle on the porous material matrix or screen of the dose diffuser. The user device may be configured to receive at least one user input related to a vaping session of the user. The user device may transmit at least one instruction to the vaporizer based on the received user input for triggering the vaping session. Similarly, a user device may be configured to receive at least one user input via a central server related to a vaping session of a user. The central server may transmit at least one instruction to the vaporizer based on the received central server input for triggering and/or managing the vaping session. The user device may also be configured to generate a session data associated with the vaping session, and the session data may be transmitted to the central server. The central server may be configured to receive the session data from the user device. The central server may be configured to modify a vaping session of a user based, at least in part, on vaping session data. The central server may update a user profile based on the session data. The user profile may comprise data associated with one or more vaping sessions of the user. The user device may also be configured to display a survey related to the vaping session of the user. The user device may receive a user feedback on the survey, and transmit the user feedback to the central server. The communication unit of the vaporizing device may comprise a Bluetooth Low Energy (BTLE) module, a WiFi module, or other electronic communication means. The user device may display a dosage information based on at least one of the retrieved concentrate information, the user profile, user's medical history, and the vaping session.

In another aspect, a method for managing concentrate usage of a user is disclosed. The method may comprise reading, by a control unit of a vaporizer, an identification code associated with a concentrate. The identification code may be transmitted to a user device through a communication unit of the vaporizer. A central server may receive the identification code from the user device. The central server may comprise a database storing a plurality of identification codes against a plurality of concentrate information. The central server may retrieve concentrate information corresponding the received identification code from the database. The retrieved concentrate information may be transmitted to the user device for displaying to a user.

In another aspect, a vaporizer comprising a housing is disclosed. The housing may comprise a cartridge configured to store a concentrate. The cartridge may comprise a nozzle, at one end, a smart chip with an identification code associated with the concentrate and a dosing mechanism at other end. The dosing mechanism may be adjacent to a mouthpiece, and may comprise a plunger driver, a pawl, and a plunger. A dosing wheel may actuate the dosing mechanism, wherein the dosing wheel may be rotatably engaged to the plunger driver. An oven may be adjacent to the nozzle of the cartridge, and may comprise a coil placed within a thermally resistant tube, an airflow channel in communication with ambient air and inhalation negative pressure airflow, and a dose diffuser containing a porous material matrix. A control unit may be configured to heat the coil of the oven based on at least one of a fire button, an in-line pressure sensor, a fan/IR reflector sensor, and the identification code associated with the concentrate. In an implementation, upon creation of a negative pressure by a user through inhalation at the mouthpiece, the control unit may heat the coil. The coil may be configured to vaporize an extruded concentrate. The extruded concentrate may be dispensed through the nozzle on the porous material matrix or screen of the dose diffuser after the dosing wheel is rotated by the user. Upon rotation of the dosing wheel, the plunger driver may drive the plunger within the cartridge to release a predefined quantity of the concentrate.

In an embodiment, the mouthpiece may be removable to slidably receive the cartridge within the housing. The identification code associated with the concentrate may be stored in a memory module consisting at least one of near field communication (NFC) means, QR code, barcode, smart chip (e.g., EEPROM), and radio frequency identification (RFID) tag, and wherein the memory module is communicably coupled to the control unit. The dosing mechanism may, in an alternative embodiment, be an auger delivery mechanism. The dosing wheel may be a hollow cylinder that circumscribes the plunger driver such that the rotation of the dosing wheel results in a rotation of the plunger driver. The plunger driver may be mechanically engaged with the plunger and the pawl. The plunger may be driven laterally downwards upon the rotation of the plunger driver due to the rotation of the dosing wheel by the user. The pawl may allow the rotation of the dosing wheel in either a clockwise or an anti-clockwise direction only. The dosing wheel may click upon rotation to a predefined degree providing audible feedback to a user. One click of the dosing wheel may release the predefined amount of the concentrate through the nozzle. The vaporizer may further comprise a communication unit configured to transmit the identification code to a user device, wherein the user device is configured to display information associated with the concentrate based on the identification code.

In another embodiment, the control unit may be configured to receive instructions from a user device via the communication unit to activate heating of the coil. The user device may display a dosage information based on at least one of the identification code, user's identity, user's medical history, vaping session history, and previous dosage. The vaporizer may further comprise a power source in communication with the control unit. The power source may be configured to supply electrical energy to the coil. The vaporizer may also comprise a power button located on the housing and in communication with the control unit. The power button upon being pressed by the user may allow supply of electrical energy from the power source to the coil. The vaporizer may further comprise a conduit proximal to the dose diffuser. The conduit may run adjacent the cartridge towards the mouthpiece to allow travel of the vaporized concentrate upon user inhalation. The conduit may comprise a filter located downstream for filtering the vaporized concentrate.

In various other aspects and embodiments of the present disclosure, a vaporizer is provided which enables a user to index (i.e., turn) a dosing wheel to deliver a predetermined dose of concentrate product for vaporization. The exemplary vaporizer may record and transmit data associated with a user's vaporization session with enhanced assurance of the type and amount of concentrate product delivered.

A vaporizer is provided with a cartridge, including a storage vessel, for safe containment of concentrate product. The stored concentrate, as such, is located away from heating means of the vaporizer to mitigate heat degradation of the concentrate product not intended for vaporization. The vaporizer, further, provides a dosing mechanism (e.g., dosing wheel, plunger, etc.) that couples with a plunger-driver of the cartridge. The dosing wheel is configured to be turned by a user unidirectionally (i.e., in only one direction) by use of a pawl constructed in the device to prevent the user from unwinding the cartridge and thus retracting the plunger from the cartridge vessel.

In an aspect, to insure proper dispensing of concentrate product, pawls constructed on a cartridge lock rotatably communicate with slots on the plunger to restrict bi-directional turning of the plunger-driver/plunger even when the cartridge is removed from the vaporizer. Furthermore, the pawls are concealed by the driver upon assembly, thus mitigating the ability of a user to disassemble the cartridge for refilling, tampering, and the like. In an example, the secured pawls protect a user from receiving concentrate product that is not representative of the manufactured product recorded on the smart chip.

To insure accurate dispensing and recording of concentrate product dosing (i.e., dose control/integrity), the exemplary vaporizer includes an infrared emitter and detector pair arranged on each side of the dosing wheel to record an indexed dose of concentrate product via predetermined spaced/sized slots on the dosing wheel.

In a further embodiment of the present disclosure the plunger and plunger-driver are fixedly attached to assure predetermined advancement of the plunger into the cartridge vessel when the plunger-driver is rotated by the dosing wheel. Advancement of the plunger provides a means by which to force the concentrate product contained in the vessel out of a nozzle at an end of the cartridge.

In yet another embodiment of the present disclosure, the nozzle is constructed with a tip seal, wherein the tip seal provides static closure of the nozzle port end thus protecting the integrity of the concentrate product held in the cartridge vessel from oxidation, contamination, encroachment, and the like (i.e., breach). In an aspect, the tip seal prevents leakage of the concentrate product from the cartridge vessel during, for instance, handling and/or use during vaporization. And further provides assurance of the delivered dose amount and prevention of confounding of the accuracy of measurement of the concentrate dose delivered. In another aspect, the tip seal incorporates an elastomer (TPE, silicone rubber, etc.) septum that seals against an insert in the nozzle. Upon turning of the dosing wheel, the plunger-driver assembly actuates the plunger into the cartridge vessel, and thereby causes concentrate product to forcibly deform the elastomer septum away from the insert, thus allowing the concentrate to extrude through the tip seal and nozzle port onto a diffuser.

In a further embodiment of the present disclosure, the vaporizer may include a vapor detection system to assess whether extruded concentrate product has been fully vaporized. An IR emitter and detector pair communicatively operate to determine whether concentrate product vapor as a result of user inhalation is present in a conduit (i.e., airpath). The vaporizer, further, informs the user via an LED lighting display whether a vaporized concentrate product dose has been completed, while also providing data regarding the session via signal transmission to the system network. The exemplary vaporizer may also provide information (e.g., graphical) generated from the data to a user via mobile device, computer, etc. regarding the vaporization session.

In yet a further embodiment of the present disclosure, a predetermined amount of doses is recorded on a cartridge via smart chip. The exemplary vaporizer, upon indexing (i.e., turning) of the dose wheel writes/updates data onto the smart chip regarding the remaining doses in the cartridge. Upon exhaustion/completion of original predetermined amount of concentrate product, the vaporizer provides information to the network (i.e., mobile device, laptop, computer, etc.) and user via LED light or other device signal that the vaporizer cartridge is depleted. At depletion, the exemplary vaporizer may restrict further vaporization. In an aspect, the restriction of further vaporization mitigates the cartridge from being refilled and reused.

This section is meant to introduce the concepts disclosed in the specification without being an exhaustive list of the many teachings and variations upon those teachings that are provided in the extended discussion within this document. Thus, the contents of this summary should not be read as a limit to the scope of the claims that follow.

Other systems, methods, features, and advantages of the present invention will be or will become apparent to one with skill in the art upon examination of the following figures and detailed description. It is intended that all such additional systems, methods, features, and advantages be included within the scope of and be protected by the accompanying claims.

BRIEF DESCRIPTION OF THE DRAWINGS

While the specification concludes with claims particularly pointing out and distinctly claiming particular embodiments of the instant invention, various embodiments of the invention can be more readily understood and appreciated from the following descriptions of various embodiments of the invention when read in conjunction with the accompanying drawings in which:

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type, for example, "pawl and clicker", or "smart chip and EEPROM". However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

The exemplary embodiments described herein are provided for illustrative purposes, and are not limiting. Other exemplary embodiments are possible, and modifications may be made to the exemplary embodiments within the spirit and scope of the present disclosure. Therefore, the Detailed Description is not meant to limit the present disclosure. Rather, the scope of the present disclosure is defined only in accordance with the following claims and their equivalents.

Accordingly, a system for managing concentrate usage is disclosed. The system enables a vaporizer to record and distribute information regarding a vaping session, user, product information like name, distillate fill batch information, laboratory results, product temperature limits, among other data. The system also provides a vaporizer and cartridge that communicatively cooperate to manage dosing data integrity (e.g., dosage control, non-confounded dosing, control over breach of concentrate containment, etc.).

Figure 1:
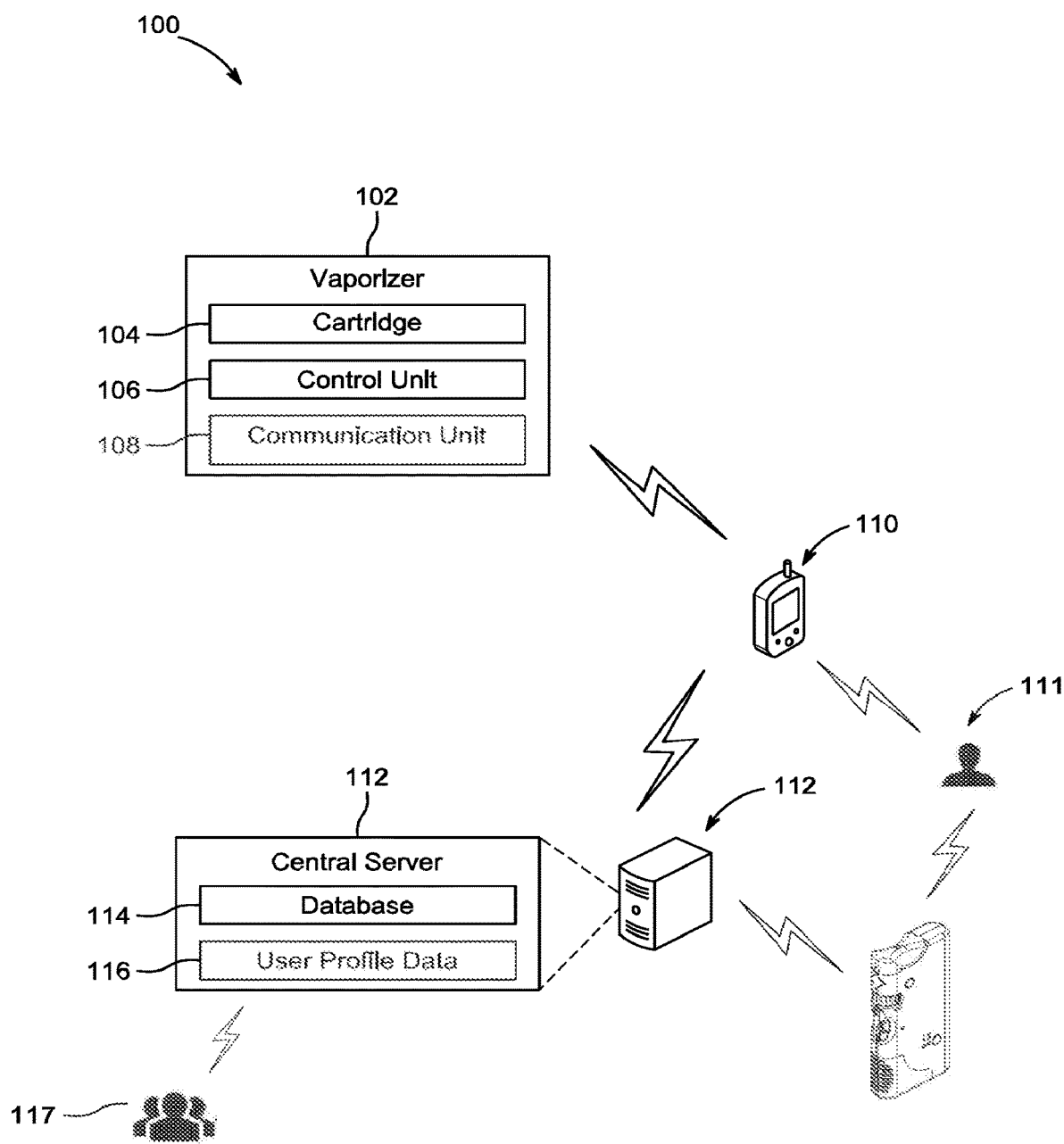
FIG. 1 illustrates a system for managing concentrate usage of a user, in accordance with an embodiment of the present disclosure.

FIG. 1 illustrates a system [100] for managing concentrate usage of a user, in accordance with an embodiment of the present disclosure. The system [100] may comprise a vaporizer [102] having a housing (not shown). The housing may comprise a cartridge [104] that may be configured to store a concentrate. The cartridge [104] may be a cylindrical container with a nozzle at one end and a dosing mechanism at another end. The nozzle [218] of the cartridge [104] may have a smart chip with an identification code associated with the concentrate. The housing of the vaporizer [102] may also comprise a control unit [106] configured to read the identification code from the nozzle [218]. The control unit [106] may also control operation of an oven of the vaporizer [102]. The oven may be adjacent to the nozzle of the cartridge [104]. A communication unit [108] may be coupled to the control unit [106], wherein the communication unit [108] may transmit the identification code to a user device [110]. In an embodiment, the user device [110] may be a mobile phone, computer, laptop, and the like, and be operable by a user [111]. The communication unit [108] of the vaporizing device [102] may comprise a Bluetooth Low Energy (BTLE) module.

The system [100] may also comprise a central server [112] comprising a database [114]. The database [114] may store a plurality of identification codes against a plurality of concentrate information. The central server [112] may be configured to receive the identification code from the user device [110]. The central server [112] may retrieve concentrate information corresponding the received identification code from the database [114]. The retrieved concentrate information may be transmitted to the user device [110]. In an implementation, the system [100] may be a public network environment including a plurality of personal computers, laptops, various servers, such as blade servers, and other computing devices. In another implementation, the system [100] may be a private network environment with a limited number of computing devices, such as personal computers, servers, laptops, and/or communication devices, such as mobile phones and smart phones. The system [100] may be operable via the central server [112] by user/users [117].

The system [100] facilitates an improved user experience by providing information about the concentrate, dosage requirement, among other things on the user device. In an embodiment, the user device [110] may be configured to receive at least one user input related to a vaping session of the user, and transmit at least one instruction to the vaporizer [102] based on the received user input for triggering the vaping session. In another embodiment, the user device [110] may be configured to generate a session data associated with the vaping session, and transmit the session data to the central server [112]. The central server [112] may also be configured to receive the session data from the user device. The central server [112] may update a user profile [116] based on the session data. The user profile [116] may comprise data associated with one or more vaping sessions of the user.

In another embodiment, the user device [110] may be configured to display a survey related to the vaping session of the user. The user could provide his/her feedback on the survey, and the user device [110] may transmit the user feedback to the central server [112]. The user device [110] may display a dosage information based on at least one of the retrieved concentrate information, the user profile [116], user's medical history, and the vaping session.

In yet another embodiment, the user device [110] may be configured to capture data from a health/biometric data capture device (e.g., AliveCor's Kardia|Omron) and the user device [110] may transmit the health-biometric data to the central server [112].

Since, the user device [110] provides information about dosage, the user is enabled with an option to deliberately select his/her dose (micro-dosing). Further, the system [100] may provide the user notification that they have completed the inhalation of the administered dose or desired amount of concentrate product.

In an aspect, a vaporizer with on-demand heating, usage tracking, improved user experience, modular components, and that which can be easily cleaned is disclosed. The vaporizer may have a housing to contain various components. The housing may comprise a cartridge configured to store a concentrate. The cartridge may comprise a nozzle at one end and a dosing mechanism at another end. The nozzle may have a smart chip with an identification code associated with the concentrate. The dosing mechanism may be adjacent to a mouthpiece, and the dosing mechanism may comprise a plunger driver, a pawl, and a plunger. A dosing wheel may actuate the dosing mechanism. The dosing wheel may be situated partially outside the housing for a user to manipulate, wherein the dosing wheel may be rotatably engaged to the plunger driver. An oven may be placed adjacent to the nozzle of the cartridge or elsewhere within the vaporizer, and the oven may comprise a coil placed within a thermally resistant tube, an airflow channel in communication with ambient air and inhalation negative pressure airflow, and a dose diffuser containing a porous material matrix. A control unit may be configured to heat the coil of the oven based on at least one of an in-line pressure sensor, a fan/IR reflector sensor, and the identification code associated with the concentrate.

In an embodiment, upon creation of a negative pressure by a user through inhalation at the mouthpiece, the control unit may heat the coil. The coil may be configured to vaporize an extruded concentrate. The extruded concentrate may be dispensed through the nozzle on the porous material matrix (or similar screen) of the dose diffuser. When the dosing wheel is rotated by the user, the plunger driver drives the plunger within the cartridge to release a predefined quantity of the concentrate.

Figure 2:
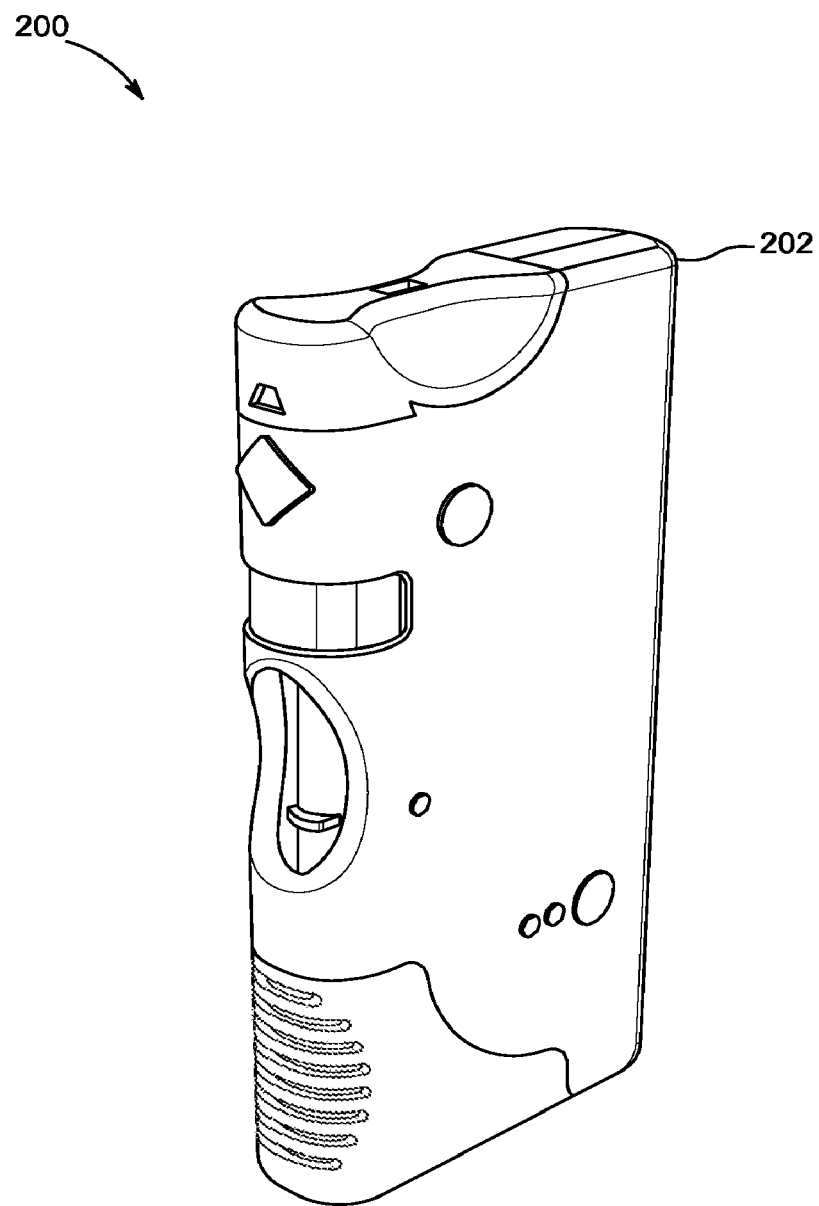
FIG. 2 is a side perspective view of a vaporizer, in accordance with an embodiment of the present disclosure.
Figure 3:
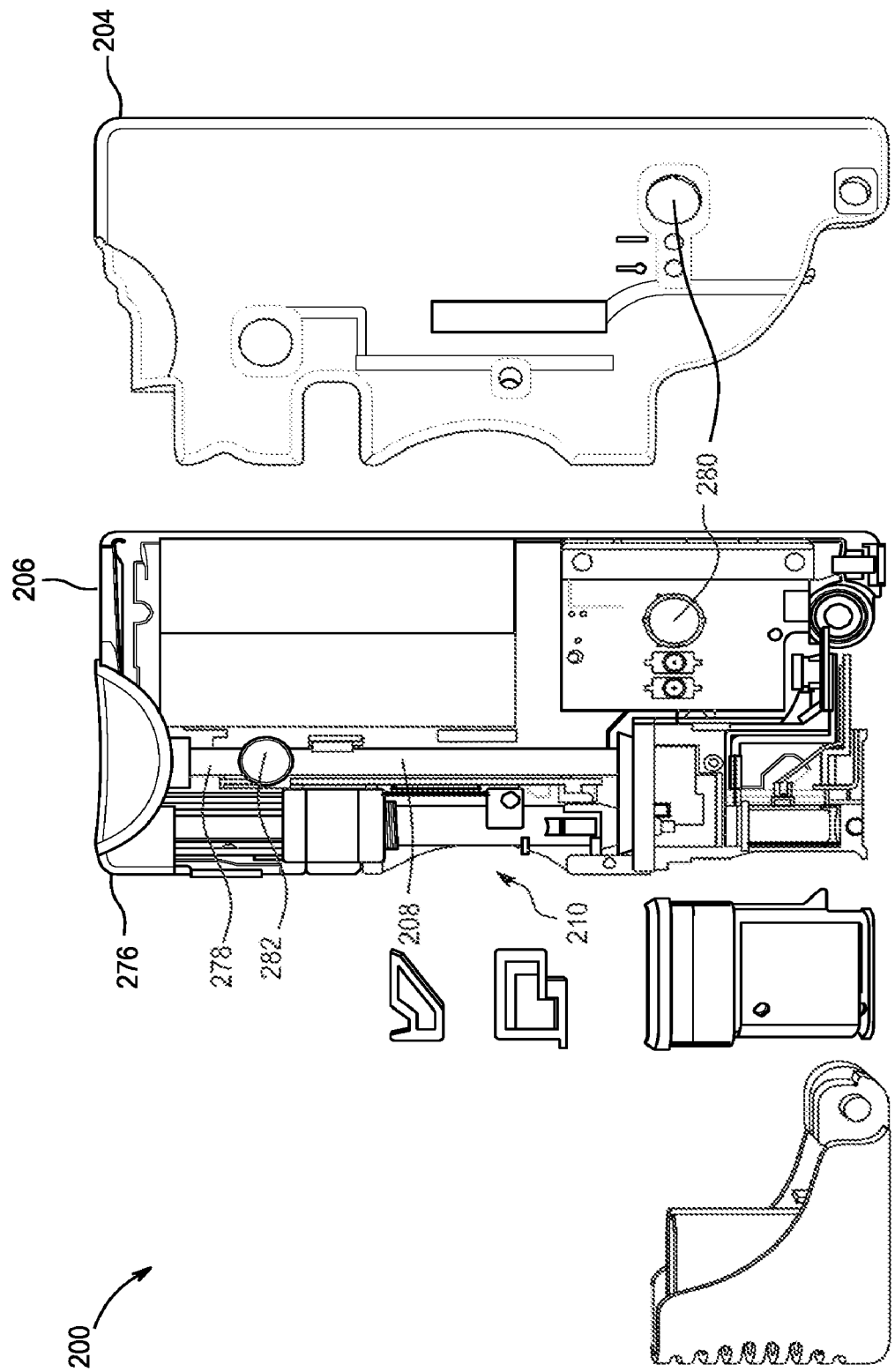
FIG. 3 is a partially disassembled view of the vaporizer, in accordance with an embodiment of the present disclosure.
Figure 4:
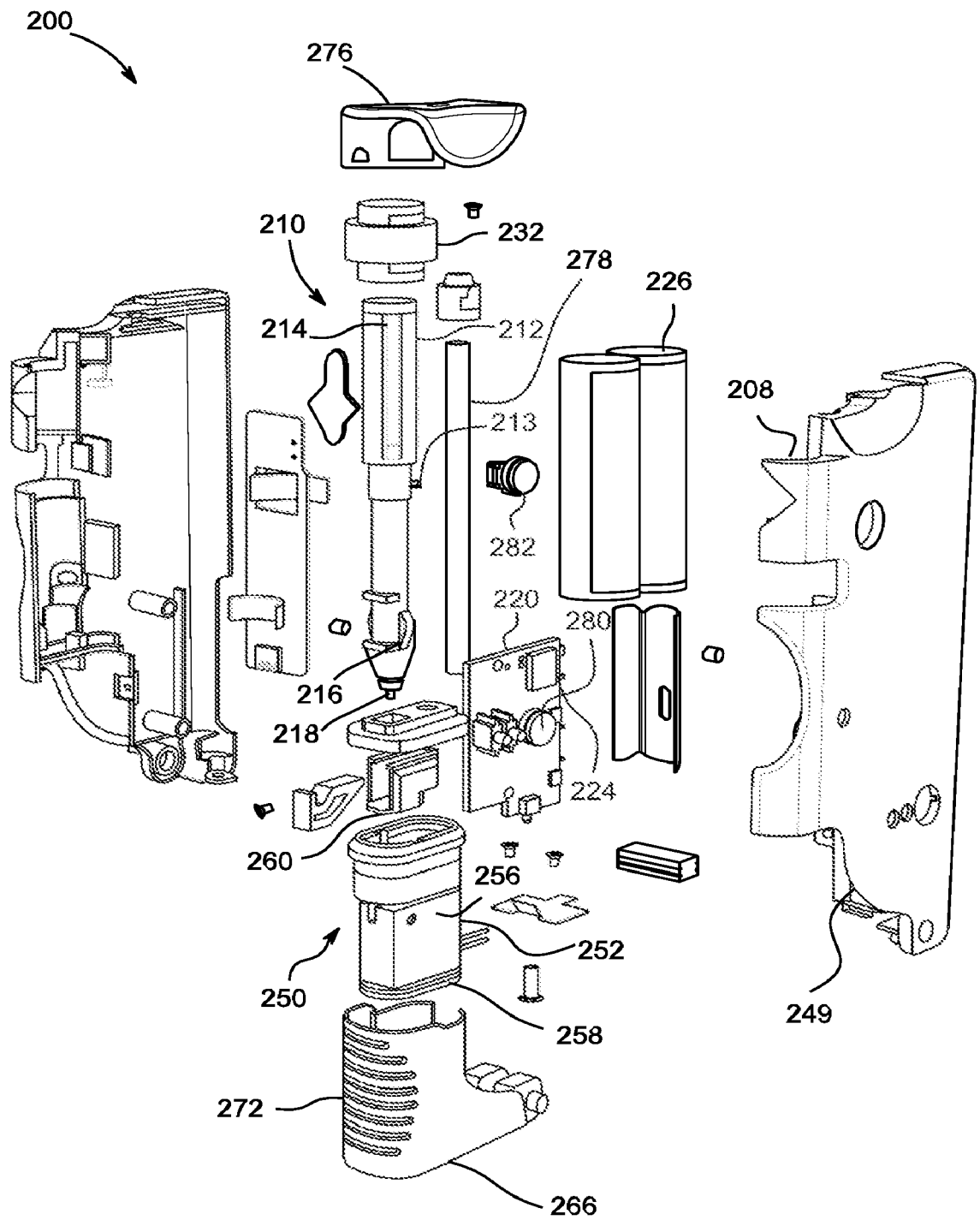
FIGS. 4 and 5 are exploded perspective views of the vaporizing device from different angles, in accordance with an embodiment of the present disclosure.
Figure 5:
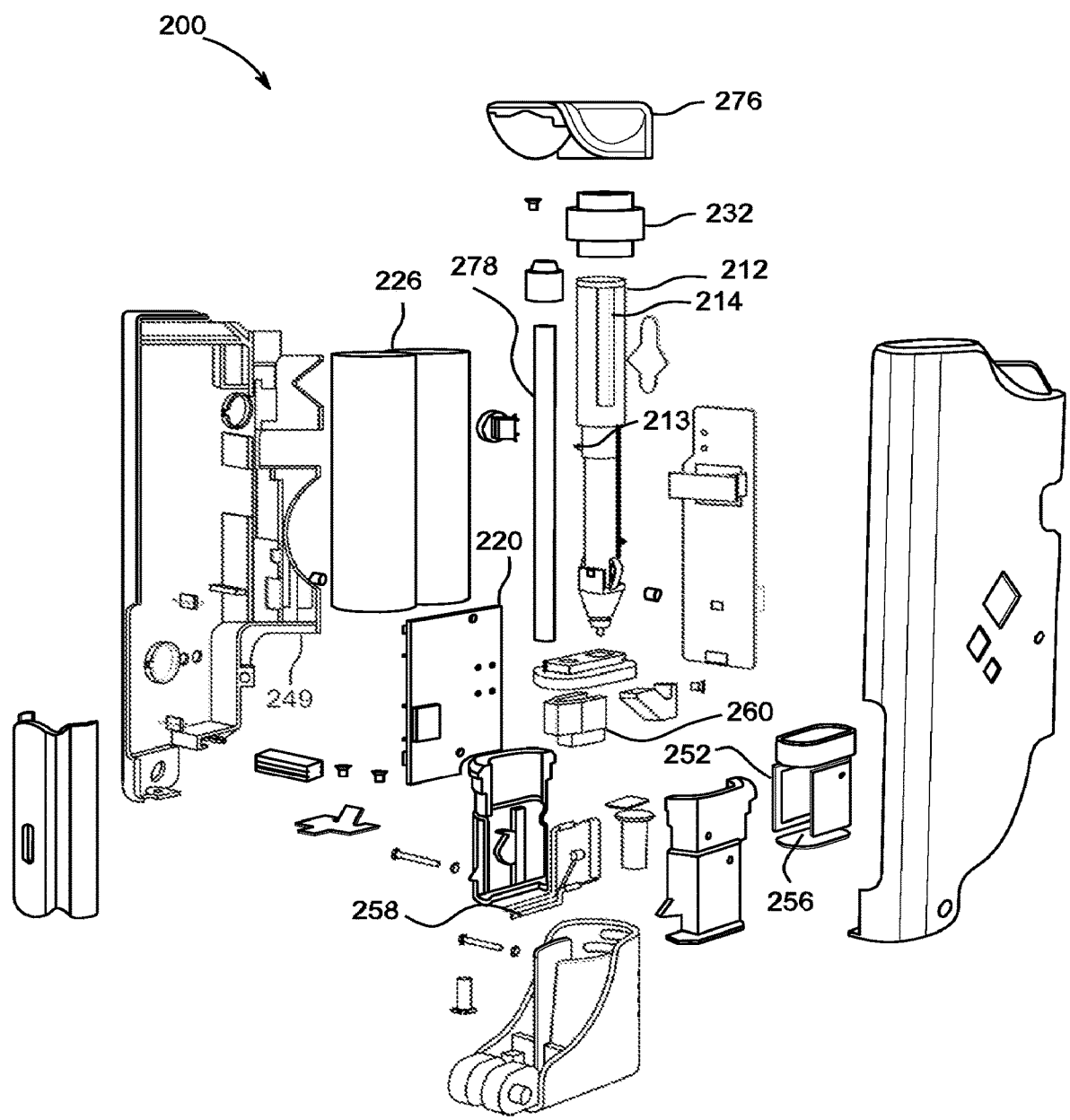

FIGS. 2-5 illustrate different views of a vaporizer [200], according to an embodiment of the present disclosure. In particular, FIG. 2 illustrates an assembled view of the vaporizer [200], and FIG. 3 illustrates a partially disassembled view of the vaporizer [200] showing the internal components thereof and further demonstrates an exemplary manner in which each component may be coupled to an adjacent component to assemble the vaporizer [200]. Further, FIG. 4 and FIG. 5 illustrate exploded perspective views of the vaporizing device 200 from two different angles. In the exploded views of FIG. 4 and FIG. 5, some assemblies are shown exploded in one figure and other assemblies are shown exploded in other figure for the purpose of illustration. Referring to FIGS. 2-5 in combination, as illustrated, the vaporizer [200] includes a housing [202] enclosing various assemblies and components thereof. The housing [202], generally, has a rectangular cross-section and extends in a longitudinal direction, imparting the housing [202] a cuboidal shape. However, it may be contemplated that the housing [202] may have other shapes, such as cylindrical, spherical, and the like. The housing [202] may be shaped such that the vaporizer [200] may be ergonomically handled by the user. The housing [202] may be manufactured from a metallic material or other material with sufficient electric conductivity and chemical resistance. In an example, the housing [202] is made of an aluminum alloy or magnesium alloy.

In an aspect, the housing [202] may include two halves, a first half [204] and a second half [206]. The two halves [204], [206] may provide multiple grooves and apertures therein, to receive and mount components of the vaporizer [200] inside the housing [202]. The two halves [204], [206] may be joined together by using fasteners, such as screws or the like. In particular, it may be seen from the associated drawings, the housing [202] may provide a groove [208] at a junction of the first half [204] and the second half [206].

The vaporizing device [200] utilizes a cartridge [210] to store a concentrate (not shown) to be vaporized. The cartridge [210], generally, includes a predefined quantity of the concentrate stored therein. The cartridge [210] may be in the form of a hollow vessel having an appropriate internal volume to be filled with the predefined quantity of the concentrate. In an example, the cartridge [210] is prefilled with 1000 mg of the concentrate. The term "concentrate," as used herein, may include substances in the form of chemicals, distillates, and isolates. Examples of the concentrate include vaporizable medications, such as tetrahydrocannabinol (THC), terpenes, cannabidiol (CBD), and other constituents of cannabinoids. Other examples of the concentrate include dry herbs, essential oils, waxes, and loose leaves. The cartridge [210] may generally be filled with a homogenous concentrate in liquid form, or a viscous liquid, such as waxes and oils, which may be extruded out of the cartridge [210] from a bottom opening (not shown) of the cartridge [210]. The cartridge [210] may include a cartridge casing, a concentrate storage vessel [211], a plunger driver [212] and a plunger [214] slidably received within the cartridge casing. The plunger [214] may be disposed inside the cartridge [210] casing in a manner such that when the plunger driver [212] is rotated, the plunger [214] is pushed laterally downwards in the cartridge [210] to force the concentrate towards the bottom opening of the cartridge [210] to be extruded out.

In an embodiment, the cartridge [210] includes a memory module [216] to store an identification code associated with the concentrate. The memory module [216] may be mounted externally on the cartridge casing. In an example, the memory module [216] may be at least one of near field communication (NFC) means, QR code, barcode, smart chip, and radio frequency identification (RFID) tag. The smart chip allows for its contents to be erased and reprogrammed using a pulsed voltage. In the present example, the identification code stored in the memory module [216] of the cartridge [210] is indicative of properties of the concentrate therein, such as type of concentrate, quantity of concentrate, expiry date of concentrate (if any), etc. In other words, the identification code associated with the cartridge [210] correlates with concentrate information. The identification code may be numeric or alpha-numeric in form. It may be understood that the identification code is programmed into the memory module [216] based on the testing of the concentrate substance in a testing facility; and each identification code may be unique to a particular batch of concentrate. As the identification code is stored in the memory module [216] of the cartridge [210], simultaneously the same identification code along with the corresponding concentrate information is stored in a database of the central server [112], as will be described later in detail.

In the vaporizer [200], the cartridge [210] is mounted in the housing [202] in a detachable manner. In particular, the cartridge [210] is received and secured in the groove [208] of the housing [202]. The cartridge [210] may have any suitable shape including, but not limited to, rectangular, cylindrical, and the like. The cartridge [210], or in particular the cartridge casing, may generally be shaped to complement the groove [208] in the housing [202] so that the cartridge [210] may snap into place inside the groove [208]. In some examples, the cartridge [210] may store a digital rights management (DRM) code, in the memory module [216], indicating whether the cartridge [210] is properly compatible to be installed in the vaporizer [200] As illustrated, the vaporizer [200] may include a nozzle [218] at one end of the cartridge [210]. The nozzle [218] may be configured be exit of the concentrate from the cartridge [210].

In an embodiment, the vaporizer [200] includes a control unit [220] to execute various instructions related to the operations of the vaporizer [200], and further to record the various operations of the vaporizer [200] and generate corresponding data. The control unit [220] may include a circuit board to which various electronic components of the vaporizer [200] are either embedded onto or connected via wires. The control unit [220] may include a processor for executing various instructions for controlling the operation of the vaporizer [200]. The processor may be a single processing unit or a number of processing units working in conjunction. The control unit [220] may further include, but not limited to, an arithmetic logic unit (ALU), a digital signal processor, a microcomputer, a field programmable gate array (FPGA), a System-on-Chip (SoC), a programmable logic unit, or any other circuitries capable of responding to and executing instructions in a defined manner. The control unit [220] may also include a memory to store instructions for executing the operations of the vaporizer [200], and further temporarily store data generated from the operations of the vaporizer [200].

In an embodiment, the control unit [220] may include a code circuitry positioned proximal to the memory module [216] of the cartridge [210], when mounted in the housing [202]. The code circuitry of the control unit [220] reads the identification code from the cartridge [210]. In an example, the code circuitry may utilize communication standards like Near Field Communication (NFC) or the like, to read the identification code from the memory module [216]. In some examples, the code circuitry may utilize laser beams or some other form of light source, to read the identification codes in the visual forms, such as bar codes, QR codes, etc. The control unit [220] may use the identification code read from the cartridge [210] for further processing, as will be explained later in detail.

In an embodiment, the vaporizer [200] includes a communication unit [224] disposed within the housing [202]. The communication unit [224] is coupled with the control unit [220] to receive and send information about the vaporizer's operation settings, among others. The communication unit [224] configures the control unit [220] of the vaporizer [200] to be in signal communication with the user device [110]. In particular, the communication unit [224] transmits the identification code read from the cartridge [210] to the user device [110]. In an example, the communication unit [224] is a Bluetooth Low Energy (BTLE) module, utilizing a relatively low-power 2.4 GHz antenna (not shown) to provide a direct link for wireless communication between the vaporizer [200] and the user device [110].

The vaporizing device 200 also includes a power source [226] to provide electrical power to various components thereof. The power source [226] may be in the form a rechargeable battery or batteries disposed within the housing [202]. The vaporizer [200] may also include a charging port (not shown) provided on an outer periphery of the housing [202] and in electric connection with the power source [226] located therein. In such case, the user may employ an external power cord (not shown) to connect the charging port with an external power socket or the like. In an example, the charging port may use a USB standard for the purpose of charging the power source [226]. In an exemplary implementation, the same charging port may further be utilized for data transfer, such as for updating a source code in the memory of the control unit [220], e.g. to change some parameters associated with the operations of the vaporizer [200]. In alternate examples, the vaporizer [200] may include a permanently fixed and retractable electrical cord in contact with the power source [226] at one end, and with another end having a plug which may be inserted in an electric socket for charging purposes.

The vaporizer [200] further includes a dosing wheel [232], generally, at a top of the cartridge [210]. The dosing wheel [232] may be rotatably disposed within the housing [202]. The dosing wheel [232] may be situated partially outside the housing [202] for a user to manipulate, wherein the dosing wheel [232] may be rotatably engaged to the plunger driver [202]. As illustrated, the cartridge [210] may have nozzle [218] and dosing mechanism at other end. The nozzle [218] may have a septum [603] at the nozzle tip to control the flow of concentrate of varying viscosities (See FIGS. 8B and 8C). The dosing mechanism may comprise the plunger driver [212], the plunger [214], and a pawl [213]. When the dosing wheel [232] is rotated by the user and the plunger driver [212] drives the plunger [214] within the cartridge [210] to release a predefined quantity of the concentrate.

In an embodiment, the dosing wheel [232] is a hollow cylinder that circumscribes the plunger driver [212] such that the rotation of the dosing wheel [232] results in a rotation of the plunger driver [212]. The plunger driver [212] may be mechanically engaged with the plunger [214] and the pawl [213]. The pawl [213] may allow the rotation of the dosing wheel [232] in either clockwise or anti-clockwise direction. The dosing wheel [232] clicks upon rotation to a predefined degree. One click of the dosing wheel [232] may releases the predefined amount of the concentrate through the nozzle [218].

The plunger driver [212] may be configured to directly correlate the rotational movement of the dispensing wheel [232] with the linear movement of the plunger [214]; i.e., for a definite degree of rotation of the dispensing wheel [232], the plunger [214] moves a certain distance depending upon a pitch of the engaged threads among other factors. This way the dosing mechanism enables the user to control the quantity of the extruded concentrate by controlling the rotation of the dispensing wheel [232].

In an alternative embodiment, the dosing mechanism may be an auger delivery mechanism.

In one or more examples, a dosing circuitry may be disposed in communication with the control unit [220], working in conjunction therewith. In some examples, the dosing circuitry may form a part of the control unit [220]. The control unit [220] may receive the information about the number of dosages of concentrate extruded from the cartridge [210] from the dosing circuitry. The control unit [220] registers a single dosage of concentrate extruded from the cartridge [210] based on the generation of a dosage signal. The control unit [220] further records a number of dosages of concentrate extruded from the cartridge [210] and utilize the code circuitry to write/program this information onto the memory module [216] of the cartridge [210], in order to track the quantity of concentrate remaining inside the cartridge [210]. Accordingly, it may be possible to find out the quantity of concentrate remaining inside the cartridge [210] detached from the housing [202] of the vaporizer [200], e.g. by the user or in a cartridge re-filling facility, using any suitable reader.

From FIGS. 2-5, it may be seen that the housing [202] may have a cut-out [249] in the form of an arc, at a bottom corner thereof. In an embodiment, the vaporizer [200] may include an oven [250] positioned in the cut-out [249]. The oven [250] may be connected with the housing [202] by using a suitable fastening arrangement, involving one or more of screws, pins, nuts and bolts, and the like. The oven

[250] includes an oven casing [252], shown assembled in FIG. 4 and disassembled in FIG. 5. The oven [250] may further include a coil [258] disposed inside in the oven casing [252].

As illustrated, the oven [250] may be located directly below the nozzle [218], and disposed in fluid communication with the cartridge [210] via the nozzle [218]. The oven [250] may comprise the coil [258] placed within a thermally resistant tube, an airflow channel in communication with ambient air and inhalation negative pressure airflow, and a dose diffuser [260] containing a porous material matrix. The dose diffuser [260] may be positioned so as to collect the concentrate extruded from the cartridge [210]. Further, the coil [258] may be positioned below the oven [250], and disposed in thermal communication therewith. The coil [258] may be configured to generate heat energy to vaporize the concentrate in the dose diffuser [260]. In an example, the coil [258] enclosed in the thermally resistant tube and having two legs connected to the power source [226] via contacts and wire running inside the housing [202].

Using these electrical connections, the coil [258] receives electrical energy from the power source [226], which in turn is converted into heat energy. In one or more examples, the coil [258] may be connected to the power source [226] via the control unit [220], such that the electrical energy supplied to the coil [258] from the power source [226] is controlled by the control unit [220]. Such configuration enables the control unit [220] to regulate the heat energy generated by the coil [258] as per a temperature setting of the vaporizer [200]. In an embodiment, the control unit [220] may be configured to heat the coil [258] of the oven [250] based on at least one of an in-line pressure sensor, a fan/IR reflector sensor, and the identification code associated with the concentrate.

In an example, the oven casing [252] may be made of a ceramic material, such as, but not limited to zirconium. Such ceramic material for the oven casing [252] may trap the heat generated by the coil [258] for efficient vaporizing of the concentrate in the dose diffuser [260], and further provide thermal insulation for outside of the oven casing [252]. In an example, the porous material matrix may be a screen (e.g., gold-plated metal mesh) or made of a metal alloy material like stainless steel, also commonly known as metal foam. The porous material matrix contains the concentrate collected within the dose diffuser [260] with its absorbing characteristics. The porous material matrix may further be structured to allow air to pass therethrough.

In an example, the vaporizer [200] provides a double-filtration system. For this purpose, the oven [250] may include a filtering means located downstream of the oven [250] Generally, the filtering means may be made of the same material as the porous material matrix. It may be understood that the vaporized concentrate is passed through the filtering means before being supplied for inhalation by the user to remove any toxic substances from the smoke and thereby providing the user with relatively cleaner vaporized concentrate for inhalation.

In an embodiment, the oven [250] may further include an oven cover [266] connected to the housing [202] using one or more magnets. In one example, the housing [202] may include a magnet and the oven cover [266] may be constructed using a magnetic plate (e.g., stainless steel plate) such that the magnet in the housing [202] and the magnetic plate of the oven cover [266] attract each other to lock the oven cover [266] with the housing [202]. In another example, the oven cover [266] may include a first set of magnets, and the housing [202] may include a second set of magnets with one magnet each for the two halves [204, 206] such that the first set of magnets and the second set of magnets attract each other to lock the oven cover [266] with the housing [202]. Further, the first set of magnets and the second set of magnets may be separated by some external pulling force, for example as provided by the user. This way the oven cover [266] is configured to move between a closed position and an open position. In the closed position, the oven cover [266] may at least partially enclose the oven [250], including the dose diffuser [260] and the coil [258], therein. In the open position, the oven cover [266] may be disposed at an angle of approximately 45° with respect to the housing [202], and allow for access to the dose diffuser [260]. The oven [250] may also include an interlock switch disposed in communication with the control unit [220]. The interlock switch generates a safety signal if the oven cover [266] is displaced from the closed position. Further, the control unit [220] receives the safety signal and may shut-off the coil [258] based on the safety signal. In an alternate example, the oven cover [266] may be connected to the housing [202] by means of a latch and a compression spring (not shown). The latch and the compression spring arrangement not only provides the hinged connection between the oven cover [266] and the housing [202], but also allows the oven cover [266] to stay in the open position, e.g. when the user may have pulled the oven cover [266] to be in the open position for accessing the dose diffuser [260].

Also, as illustrated, the oven cover [266] may include a plurality of vents [272] at its sides and bottom (not shown). Further, in the oven [250], the oven casing [252] may include a plurality of vents therein. The vents may allow entry of fresh air from the atmosphere into the oven [250] to be circulated in a defined path inside the vaporizer [200]. The air received in the oven [250] is exposed to the coil [258], which in turn heats the received air. In one example, the coil [258] heats the air. Particularly, the air may be superheated. This superheated air is received in a vaporization chamber [256] through the orifices in the dose diffuser [260]. The heated air, in the vaporization chamber [256], passes through the porous material matrix, thereby vaporizing the concentrate absorbed in the dose diffuser [260] by the convection effect.

The vaporizing device 200 may include a mouthpiece [276] to administer the vaporized concentrate to the user. The mouthpiece [276] may, typically, be made of any medical grade material, such as silicone, soft rubber, and plastic. In an example, the mouthpiece [276] may be detachably mounted to the housing [202] of the vaporizer [200]. The mouthpiece [276] may, generally, be located at a top end of the housing [202]. The vaporizer [200] may further include a conduit [278] fluidly communicating the mouthpiece [276] with the vaporization chamber [256] or dose diffuser [260]. As may be understood, the conduit [278] provides a path inside the vaporizer [200] for the flow of air from the vaporization chamber [256] or dose diffuser [260] to the mouthpiece [276]. Therefore, as the user pulls for the vapors through the mouthpiece [276], the fresh air is drawn into the oven [250] via the vent [272], which carry the vaporized concentrate from the vaporization chamber [256] to the mouthpiece [276] via the conduit [278] for consumption by the user. It may be contemplated that such configuration of vents in relation to the conduit [278] allows for a cross-flow through the oven [250] to facilitate drawing of the air from outside of the vaporizer [200] The conduit [278] may further help to substantially isolate the path for flow of the vaporized concentrate from the electronic components of the vaporizer [200] in order to avoid possibility of any short-circuits.

In another configuration, the vaporizer [200] further allows for manual loading of the concentrate directly into the vaporization chamber [256]. For this purpose, the user may put the oven cover [266] in the open position such that the vaporization chamber [256] is accessible. In case of a liquid concentrate, the user may directly pour or inject the concentrate onto the porous material matrix to be absorbed thereby. In case of a non-liquid concentrate, such as wax, powder, dry *cannabis*, etc., the user may first remove the porous material matrix from the vaporization chamber [256], and then place the concentrate directly. In some other cases, the user may obtain a dose diffuser prefilled with pods of dry-herb or the like, and directly place such dose diffuser inside the vaporization chamber without the porous material matrix; thus providing convenient usage of non-liquid concentrate. In any case, the heated air from the coil vaporizes the concentrate for consumption purposes. In other examples, the cartridge may be designed to store and extrude the non-liquid concentrate into the vaporization chamber.

It may be contemplated that the vaporizer [200] may accrue vapor residue on specific internal components, especially the conduit [278], as a result of repetitive use, even when used properly. In order to clean the conduit [278], the user may; first remove the mouthpiece [276], and then pull the oven cover [266] to overcome the attractive force of the magnets such that the oven cover [266] is moved to its open position. At this point, the user may dip a pipe cleaner (not shown) in a cleaning solution. It may be contemplated that the pipe cleaner may be a Q-tip or the like. The user may use this pipe cleaner with the cleaning solution and slide the pipe cleaner down through the top of the conduit [278] until it comes out the bottom thereof. The user may repeat the above steps until the conduit [278] is completely clean. Further, to clean the vaporization chamber [256], the user may; first remove any loose particulate or residual substance present therein, and then remove the porous material matrix or screen and the dose diffuser [260] from the bottom of the vaporization chamber [256]. The user may then use a Q-tip dipped in the cleaning solution and gently wipe off the residue accrued in the vaporization chamber [256]. It may be contemplated that the use of dose diffuser [260] reduces the need of frequent cleaning of the vaporization chamber [256], as the residues from the concentrate and excess accumulation from the vaporization builds on the dose diffuser [260] rather than the walls of the vaporization chamber [256], and further allows easier cleaning as the dose diffuser [260] may be removed from the vaporization chamber [256] for its cleaning by moving the oven cover [266] in the open position. In order to clean the porous material matrix, the user may; first make sure to remove the dose diffuser [260] including the porous material matrix from the vaporization chamber [256], then soak the porous material matrix in the cleaning solution for about 15 minutes and then rinse thoroughly with water, then let the porous material matrix to dry, and reinstall. Similarly, to clean the mouthpiece [276], the user may; first make sure to remove the mouthpiece [276] from the housing [202] by gently pulling it off of the top of the conduit [278], then soak the mouthpiece [276] in the cleaning solution for about 15 minutes and then rinse thoroughly with water, then let the mouthpiece [276] to dry, and reinstall the mouthpiece [276] back in the vaporizer [200].

In some embodiments, the vaporizer [200] may include one or more buttons to control one or more user-controlled operations thereof. The vaporizer [200] may further include one or more indication lights for communicating information about the various operations and current settings/parameters of the vaporizer [200]. In an example, the indication lights may be RGB based LEDs. In the illustrated example, the vaporizer [200] is shown to include two buttons; a power button [280] and a fire button [282]; and further four indication lights namely, a first indication light, a second indication light, a third indication light and a fourth indication light. In the vaporizer [200], each of the buttons may generate specific signals on pressing and are disposed in signal communication with the control unit [220]; such that the control unit [220], acting as the intermediator, may generate specific instructions in response to such signals for signaling the corresponding components to perform certain functions. Further, the control unit [220] may control the flashing of the indication lights to convey specific information to the user, as programmed. As illustrated, some of the buttons and the indication lights, specifically the power button [280], and the second indication light and the third indication light are directly embedded on the circuit board of the control unit [220].

In one exemplary configuration, the user may hold the power button [280] for 2 seconds, to turn the vaporizer [200] ON/OFF. In an example, the communication unit [224] of the vaporizer [200] starts pairing with the user device [110] as soon as the vaporizer [200] is turned ON. Further, the second indication light may flash while pairing between the communication unit [224] and the user device [110] takes place, and then show solid BLUE color when the pairing process is completed. The power button [280] may further be used for checking various current settings of the vaporizer [200] For example, clicking the power button [280] once may show the charge level of the power source [226] using the second indication light; two clicks may operate the third indication light to indicate temperature setting, and three clicks may restart the communication unit [224] to re-establish a connection with the user device [110] and may further flash all the lights once. The fire button [282] may be used for operating the coil [258], in the vaporizer [200]. The user may press the fire button [282] and hold it down to heat up the coil [258] to the defined temperature setting and continue to hold it down while inhaling the concentrate to keep the vaporizer [200] at the defined temperature setting.

Further, in one exemplary configuration, the first indication light may be indicative of the power state of the vaporizer [200], i.e. the first indication light being ON represents that the vaporizer [200] is ON and vice-versa. Similarly, the second indication light may be indicative of the current charge level of the power source [226] of the vaporizer [200]; such as GREEN color indicates power level greater than 50%. YELLOW color indicates power level equal to or less than 50%, RED color indicates power level equal to or less than 15%, and flashing RED color indicates power level less than 5% and that the vaporizer [200] needs immediate charging for continuous operation. The third indication light may be indicative of the temperature setting of the vaporizer [200], such that GREEN color may represent high temperature setting, BLUE color may represent medium temperature setting and PURPLE color may represent low temperature setting, of the vaporizer [200]. The fourth indication light indicates various states of the vaporizer [200] using different color schemes; such as heating up, reached defined temperature setting, level of the concentrate in the cartridge [210], warning if the user is pulling too hard, etc. It may be contemplated that control schemes for the buttons [280, 282] and color schemes for the indication lights as described herein are not limiting to the disclosure.

Further, in an embodiment, the vaporizer [200] includes an anemometer to measure flow rate of a volume of air passing therethrough. In an implementation, the coil [258], as already present in the vaporizer [200], is used as the anemometer for airflow measurement purposes; and as such the terms "anemometer" and "heating element" have been interchangeably used for the description. The anemometer may, generally, be placed somewhere inside the conduit [278] in direct exposure to the airflow therein. In an example, the anemometer works on the principle of a hot wire anemometer. In the present implementation of the anemometer in the vaporizer [200], current and voltage measurements are taken directly from the heating element [258], while operating. Further, some other parameters of the coil [258] including operating temperature, material composition, and dimensionality are determined. These measurements are first used to compute the resistance of the coil [258] prior to any flow to establish a calibration offset or "baseline." As air begins to flow across the coil [258], some of the heat is imparted into the air and thus cools the coil [258] slightly. As a material's resistance is proportional to its temperature, this change in temperature leads to a measurable deviation from the baseline resistance. And as the law of Joule Heating provides that the rate of cooling is proportional to the volume of air being heated, it may be extrapolated that this deviation may be proportional the rate of flow. Therefore, it is possible to determine flow rate of the volume of air flowing through the vaporizer [200] simply by algorithmically correlating current and voltage to resistance deviations as the coil [258] operates. The air flow, as calculated, may be used to estimate the quantity of the concentrate consumed by the user in comparison to the quantity of the concentrate extruded from the cartridge [210].

In an aspect, the mouthpiece [276] is removable to slidably receive the cartridge [210] within the housing [202]. The communication unit [224] may be configured to transmit the identification code to the user device [110], wherein the user device [110] is configured to display information associated with the concentrate based on the identification code. The control unit [220] may be configured to receive instructions from the user device [110] via the communication unit [224] to activate heating of the coil [258]. In an exemplary scenario the user device [110] may display a dosage information based on at least one of the identification code, user's identity, user's medical history, and previous dosage. In another aspect a filter may be present downstream of the conduit [278] for filtering the vaporized concentrate.

The vaporizer [200] is configured to provide an airtight seal upon loading for efficiency, while also providing easier access by users to facilitate cleaning of the device before/after use to assure optimum performance.

Existing vaporizers use either combustion or convection techniques to vaporize concentrate oils. The concentrate oils' active compounds are delivered more efficiently without unhealthy levels of byproducts, such as tar (PAH) and carbon monoxide via convection, and as such, it is the vaporization method of choice. However, it is also more difficult to achieve and maintain a consistent temperature at/of the oil for efficient vaporization using conventional convection techniques. In addition, oil has a tendency to flash and wick when exposed to heat creating a loss of efficiency in current vaporizers. These systems also exhibit overheating after a few uses requiring safety circuitry to protect the user from being burned. Available vaporizers use various methods in an attempt to provide controlled convection heating to concentrate oils, including flowing hot air to oils contained in chambers with limited surface area for flashing, dispensing oils onto large dosing pads requiring excessive heat to vaporize, and batch heating more oil than is required for a dose contributing to inefficient delivery of the vapor. The vaporizer [200] employs a concentrate product oven that mitigates wicking, provides integrated components for increasing vaporization efficiency, and offers simple precision elements for micro-dosing control of vaporization product avoids the aforementioned setbacks.

Existing vaporizers exhibit a time lapse between when a user initiates the "fire" button (i.e. vaporizer device power) and when the vaporizer device is ready for the user to inhale vapor of the heated concentrate oil. Currently available vaporizers have a time lapse that can range from as much as 5 seconds to 90 seconds, depending on the device and its heating methodology. User convenience is compromised in that the time lapse requires the user to continually hold the "fire" button until the device signals that it is ready for inhalation. In addition, a user must continue to hold the "fire" button beyond the time lapse period until the desired inhalation/dose is completed. Such device operation leads to a significant waste of power and unnecessary heating of the vaporizer.

Referring to FIG. 1, a block diagram of a system 100 for managing concentrate usage of a user is illustrated, in accordance with an embodiment of the present disclosure, according to defined operational parameters, as described in the following description.

Continuing with the description of FIG. 1, in an example, the user device [300] may be a laptop, a smartphone, a mobile phone, a personal digital assistant (PDA), a tablet, a desktop computer, and the like. The user device [110] is communicatively coupled with the central server [112] through a network. The network may be a wireless network, a wired network, or a combination thereof. The network may also be an individual network or a collection of many such individual networks interconnected with each other and functioning as a single large network, e.g., the internet or an intranet. The network may be implemented as one of the different types of networks, such as intranet, local area network (LAN), wide area network (WAN), the internet, and the like.

In an example, the central server [112] may be a server, a desktop computer, a notebook, a portable computer, a workstation, a mainframe computer, and a laptop. In an implementation, the central server [112] may be a distributed or a centralized network system in which different computing devices may host one or more of the hardware or software components of the central server [112]. Further, in an example, the central server [112] may be configured as an open Application Programming Interface (API) to facilitate communication with other computer systems, such as a hospital electronic health records (EHR) system. The central server [112] includes a database [114] and user profile data [116]. The database [114] includes a plurality of identification codes and corresponding concentrate information. As described earlier, each identification code from the plurality of identification codes corresponds to a concentrate and is thus, linked with concentrate information corresponding to the concentrate. In an example, a vendor implementing the central server [112] maintains the database [114]. For instance, the vendor may use a computing device, such as the user device [110], for generating an identification code for a concentrate. Subsequently, the vendor may use the computing device to upload the identification code and concentrate information corresponding to the concentrate to the central server [116]. Further, as described earlier, for each cartridge [210] filled with the concentrate, the identification code corresponding to the concentrate is stored on the memory module [216] of the cartridge [210]. As explained in the following description, assigning the identification code to the cartridge [210] facilitates in monitoring and managing concentrate usage of the user.

In an example, a user may use the vaporizer [200] for performing one or more vaping sessions. Prior to using the vaporizer [200] for a vaping session, the user may initially register himself/herself with the vendor of the vaporizer [200]. For registration, the user may install an application associated with the vaporizing device 200 on the user device [110]. The application provides the user with a graphical user interface for accessing services and operations associated with the vaporizer [200]. For instance, the user may use the application for operating or altering one or more functions of the vaporizer [200]. In another example, the user may use the application for obtaining information about the concentrate stored in the cartridge [210]. Once the application is installed, the user device [110] is configured to record user information associated with the user. The user information may include, without limitation, a name, an age, a height, a weight, a sex, and a medical history of the user.

In an example, the user device [300] transmits the user information to the central server [112] for registering the user. As may be understood, the user information may be transmitted over a communication link implementing predetermined security protocols and standards for ensuring safety of the user information. On receiving the user information, the central server [112] may be configured to generate a user profile for the user based on the user information. As may be understood, once the user profile is generated, the user may not be required to register for subsequent vaping sessions. In an example, the user profile may be updated to include additional information besides the user information. The additional information may include session logs associated with vaping sessions of the user, information about one or more concentrates used by the user, information about efficacy of the concentrates with respect to user's reason for using a concentrate in a vaping session, and one or more recommendation for the user. In an example, the additional information is included in the user profile based on session data related to the current vaping session and the subsequent vaping sessions, as will be explained in the following description. In an example, the central server [112] stores the user profile in the user profile data [116]. In an example, the user profile data [116] may be stored in a single database (not shown). In another example, the user profile data [116] may be stored in distributed or unlinked databases (not shown) communicatively coupled to the central server [112]. In aforementioned examples, the single database or the distributed databases store(s) the user information in compliance with predefined security protocols, such as the Health Insurance Portability and Accountability Act (HIPAA).

As mentioned above, in an example, the user may learn about the concentrate being used in the cartridge [210]. In such cases, the control unit [220] is configured to read the identification code stored in the memory module [216]. On reading the identification code, the control unit [220] may trigger the communication unit [224] to transmit the identification code to the user device [110]. The communication unit [224] transmits the identification code to the user device [110] through the antenna therein. In an embodiment, the user device [110] may obtain the identification code from the user, in case of manual loading of the concentrate. For instance, the user may provide the identification code corresponding to the concentrate through a user input. In another example, the user may scan the identification code using the user device [110]. For instance, if the identification code is a bar code, the user may switch on a camera (not shown in the figure) of the user device [110] for capturing the bar code.

In an example, the user device [110] is configured to transmit the identification code to the central server [112] for obtaining the concentrate information corresponding to the concentrate. On receiving the identification code, the central server [112] is configured to retrieve the concentrate information corresponding to the identification code from the database [114]. The retrieved concentrate information is then transmitted by the central server [112] to the user device [110] for displaying the concentrate information to the user. In an alternate example, the communication unit [224], in the vaporizer [200], may be capable of directly transmitting the identification code to the central server 112. e.g., using a Wi-Fi module, a cellular module or the like. Further, the vaporizer [200] include a screen (not shown), like an e-ink display, to display the concentrate information directly on to the vaporizer [200].

The user device [110], in an example, may receive and store the concentrate information in an internal memory module (not shown) of the user device [110]. In an example, on receiving a user input for displaying the concentrate information, the user device [110] is configured to display the concentrate information to the user through a display screen (not shown) of the user device [110]. In an example the displayed concentrate information may include, a name of the concentrate, a quantity of concentrate left in the cartridge [210], and a chemical composition of the concentrate. Displaying of the concentrate information to the user enhances the user awareness with respect to the concentrate the user is using for vaping sessions. For instance, the user is made aware of the chemical composition of the concentrate. Accordingly, the user may choose to continue using the concentrate or may prefer to change the concentrate based on the chemical composition.

In an example, when a user of the vaporizer [200] seeks to perform a vaping session, the user may provide at least one user input to the user device [110]. For instance, the user may provide a user input for selecting a reason for performing the vaping session. In such a case, the user device [110] is configured to display to the user a list of reasons for performing the vaping session. The user may then select the reason from the list of reasons. In another example, the user may provide a user input defining the reason for performing the vaping session. Further, the user device [110] records the reason and may update the list of reasons to include the reason defined by the user. Additionally, the user may provide a user input for determining a quantity of the concentrate to be administered during the vaping session. In addition to determining the quantity of the concentrate to be administered, the user may operate the vaporizer [200] for extruding the determined quantity into the vaporization chamber [256]. Further, the user may provide a user input for configuring a temperature setting of the vaporizer [200]. Thereafter, the user may provide a user input for triggering the vaping session. On receiving the user input, the user device [110] is configured to transmit at least one instruction to the vaporizer [200] for triggering the vaping session.

On receiving the at least one instruction, the vaporizer [200] may configure the coil [258] to the configured temperature for vaporizing the concentrate at that temperature.

In an example, the concentrate information may also include a predetermined temperature setting depending on the type of the concentrate. Further, the control unit [220] may be configured to control the coil [258] based on the temperature setting in the concentrate information. It may be understood that the user may choose to override the predetermined temperature setting to a desired temperature setting for a particular vaping session, by providing a user input via the user device [110]. The control unit [220] may control the heat energy generated by the coil [258] based on instructions as per the user input. Once the concentrate is vaporized, the user may receive a notification indicating that the vaporizer [200] is ready for use. In an example, the notification is displayed through the first indication light on the vaporizer [200]. In another example, the notification is provided through a message on the user device [110]. In yet another example, the notification is provided through both, the first indication light and the message.

In an example, when the vaping session concludes. i.e., the user is no longer using the vaporizer [200] for vaping for a predetermined time, the user device [110] is configured to generate session data corresponding to the vaping session. In an example, the session data may include a reason for performing the vaping session, the quantity of concentrate administered to the user, and the temperature setting at which the vaping session was performed. The user device [110] subsequently, transmits the session data to the central server [112]. In an example, the central server [112] receives the session data from the user device [110]. On receiving the session data, the central server [112] is configured to update the user profile [116].

In an implementation, the user device [110] is configured to generate a user survey form related to the vaping session of the user. The user survey form, in an example, may include one or more questions related to the vaping session. For instance, the user survey form may include questions related to efficacy of the concentrate, temperature setting of the vaporizer [200], and other such questions. The user device [110] may then display the user survey form to the user. In another implementation, the central server [112] may be configured to generate the user survey form on receiving the session data and may transmit the user survey form to the user device [110] for displaying to the user. In an example, the user survey form is displayed to the user after a predetermined time interval, for instance, thirty minutes after the vaping session.

In another embodiment, the user device [110] may be configured to capture data from a health/biometric data capture device (e.g., AliveCor's Kardia|Omron) and the user device [110] may transmit and/or exchange the health/biometric data with the central server [112] or vaporizer [102].

Subsequently, the user device [110] is configured to receive a user feedback from the user based on the user survey form. In an example, the user survey form may include one or more answers to the questions included in the user survey form. Once the user feedback is received, the user device [110] transmits the user feedback to the central server [112]. The central server [112], in an example, may store the user feedback in the user profile data [116] and may associate the user feedback with the user profile of the user. In an example, the central server [112] may update the user profile based on the user feedback. For instance, the central server [112] may update the additional information based on the user feedback.

In an embodiment, the central server [112] is configured to generate recommendations for the user. For this purpose, the central server [112] identifies a plurality of users based on one or more user parameters associated with the user. The user parameters may include, without limitation, age, height and weight of the user. On identifying the plurality of users, the central server [112] is configured to retrieve user feedback associated with the plurality of users. Once the user feedback is retrieved, the central server [112] is configured to analyze the user feedback to generate a suggestion for the user. For instance, the central server [112] may identify other concentrates used by the plurality of users for a vaping session similar to the vaping session of the user. Amongst the identified other concentrates, the central server [112] may identify a concentrate in demand with other users based on the user feedback. The central server [112] may then generate the suggestion related to the concentrate. Once the central server [112] generates the recommendation, the central server [112] transmits the suggestion to the user device [110]. The user device [110] may then display the suggestion to the user. In an example, the central server [112] may further transmit the generated suggestion to a user device of a registered physician of the user.

Figure 6:
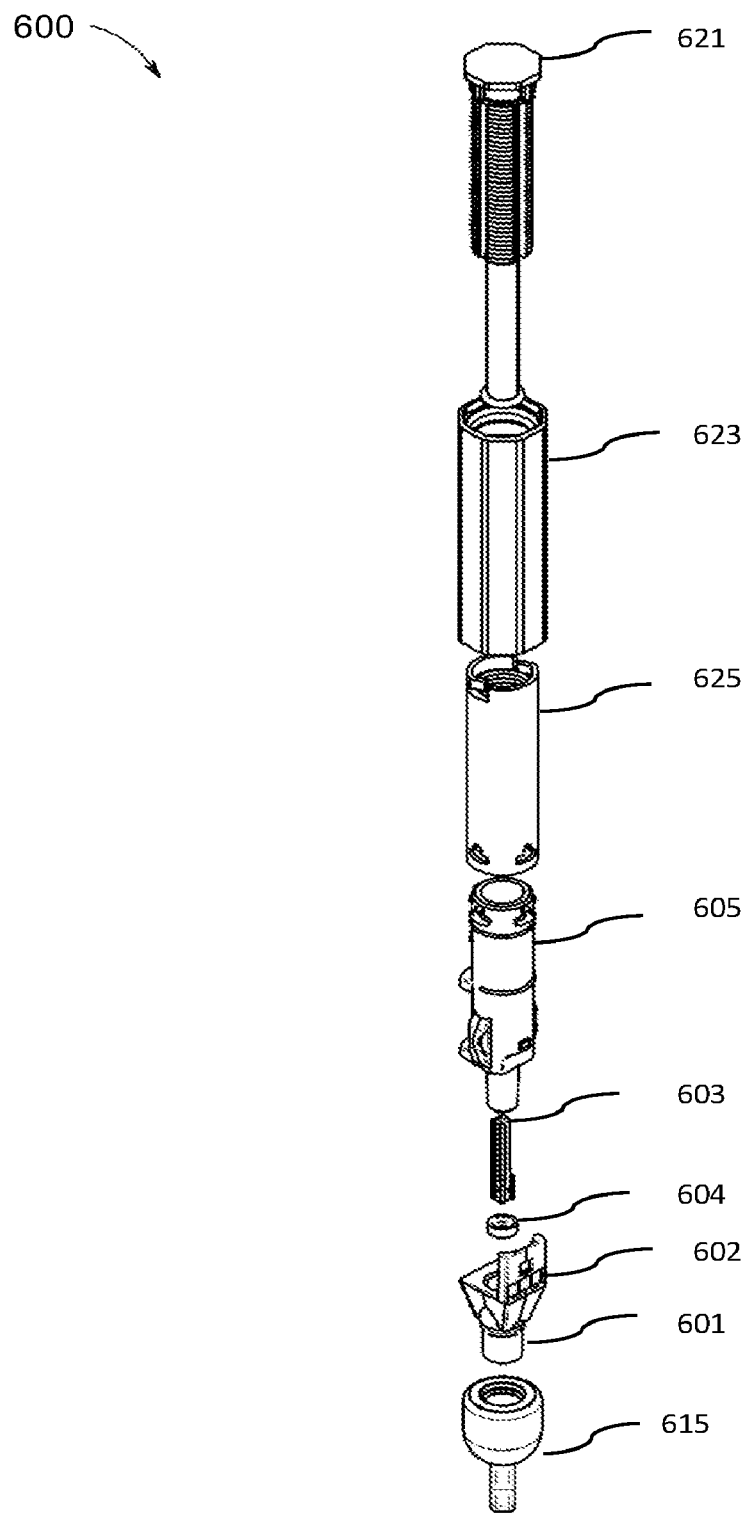
FIG. 6 is an exploded perspective view of an exemplary cartridge, in accordance with an embodiment of the present disclosure.

FIG. 6 depicts an exemplary cartridge [600] configured to store a concentrate. In an embodiment of the present disclosure, the cartridge [600] may comprise a nozzle [601], at one end, having configured thereon a smart chip [602], smart chip [602] may have an identification code associated with the concentrate. In another embodiment, exemplary cartridge [600] has assembled thereon a tip seal [603] to prevent leakage of concentrate product from the cartridge vessel [605] during, for instance, handling and/or use during vaporization.

In an aspect, the tip seal [603] incorporates septum [604] that seals against an insert in the nozzle (not shown). The septum [604] may be an elastomer (TPE, silicone rubber, etc.) or other flexible, resilient material. In a further aspect, upon turning of the dosing wheel [232], the plunger-driver assembly [212] actuates the plunger [214] into the cartridge vessel [605], and thereby causes concentrate product to forcibly deform the septum [604] away from the nozzle insert [603], and thus allow the concentrate to extrude through the tip seal [603] onto a diffuser.

In another embodiment of the present disclosure, at another end of cartridge [600] there is provided a dosing mechanism [620]. The dosing mechanism [620] may be adjacent to a mouthpiece, and comprises a plunger [621], plunger driver [623], and a cartridge lock [625]. A dosing wheel [232] may actuate the dosing mechanism [620], wherein the dosing wheel [232] is rotatably engaged to the plunger driver [623]. Upon rotation of the dosing wheel [232], the plunger driver [623] may drive the plunger [621] within the cartridge vessel [605] to release a predefined quantity of the concentrate. The dosing wheel is configured to be turned by a user [111] unidirectionally (i.e., in only one direction) by use of a pawl [904]. The pawl [904] prevent the user [111] from unwinding the cartridge and thus retracting the plunger from the cartridge vessel.

In an aspect, to insure proper dispensing of concentrate product, exemplary pawls [904] constructed on a cartridge lock [625] rotatably communicate with slots on the plunger [621] to restrict bi-directional turning of the plunger/plunger driver [621, 623] even when the cartridge [600] is removed from the vaporizer [200]. Furthermore, the pawls [904] are concealed by the plunger driver [623] upon assembly, thus mitigating the ability of a user to disassemble the cartridge [600].

In a further aspect of the present disclosure, the plunger and plunger-driver [621, 623] are fixedly attached to assure predetermined advancement of the plunger into the cartridge vessel [605] when the plunger-driver [623] is rotated by the dosing wheel [232].

Figure 7:
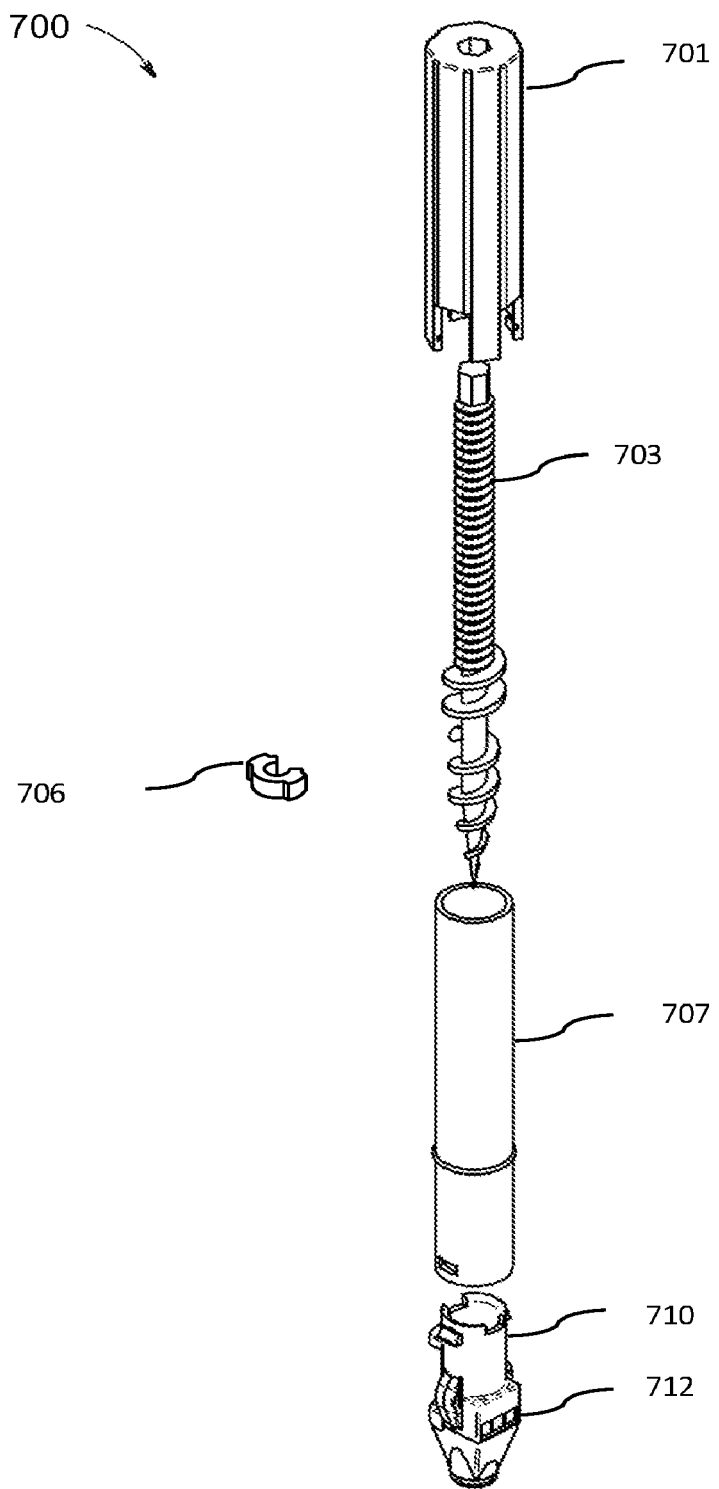
FIG. 7 is an exploded perspective view of an exemplary cartridge for dispense of a non-liquid concentrate (e.g., powder), in accordance with an embodiment of the present disclosure.

FIG. 7 depicts an alternative embodiment of a cartridge [700] configured for dispensing generally non-liquid concentrate (e.g., powder, leaf, flower, wax, etc). The exemplary cartridge [700] provides similar operation as to that of cartridge [600]. Cartridge [700] dispenses generally non-liquid concentrate (e.g., powder) by utilization of an auger [703]. Cartridge [700], comprising driver [701], nozzle [710], and smart chip [712], etc. is communicatively operable within system [100] so as to provide dose control and dose integrity data within the network.

Figure 8A:
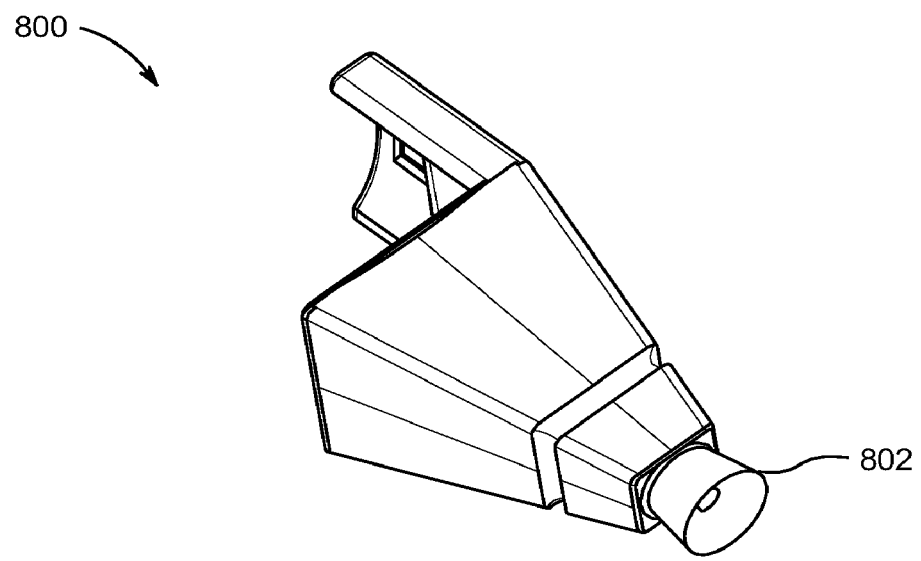
FIG. 8A is a side perspective view of the nozzle of the vaporizing device cartridge system, in accordance with an embodiment of the present disclosure.

FIG. 8A depicts an exemplary nozzle [800], according to an embodiment of the present disclosure. In an aspect of the present disclosure, the nozzle [800] is made of high temperature polymer material, such as stainless steel, polysulfone, high-temperature liquid crystal polymers (e.g., Vectran™ or PEEK), or other material that is designed to operate under continuous exposure to vaporizing temperatures (generally <550 F). In an embodiment of the present disclosure, vaporizing temperatures are controlled so as not to avoid the combustion temperature and/or denaturing of concentrate products. In an embodiment of the present disclosure, the nozzle has circumferential groove [802] to mate with an exemplary feature constructed on an oven seal seat to provide airtight seal and, as such, eliminate inflow of air into the oven during negative pressure inhalation by a user. In an aspect, the nozzle [800] is constructed with a stepped and flared feature [802] at the nozzle exit to mitigate wicking of oil-based concentrate product up the nozzle.

Figure 8B:
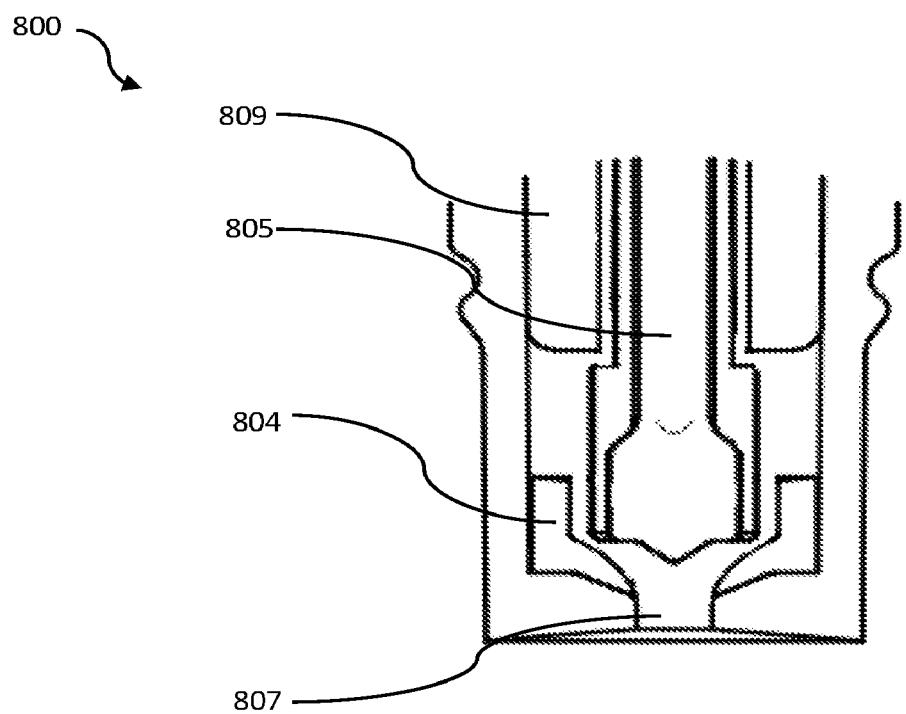
FIG. 8B is a front elevational view of the nozzle of the vaporizing device cartridge system illustrating a septum in an open position, in accordance with an embodiment of the present disclosure.
Figure 8C:
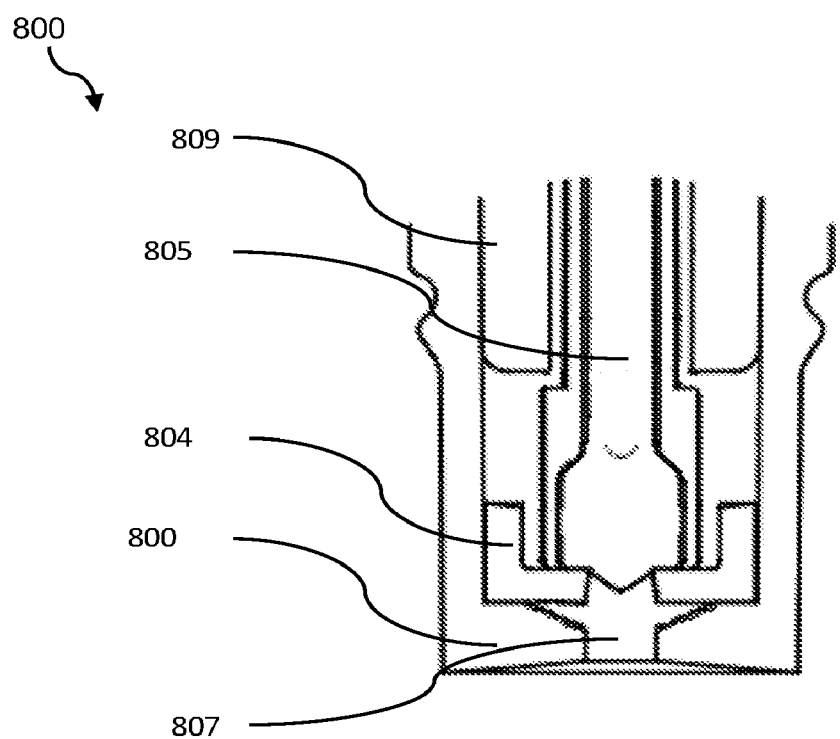
FIG. 8C is a front elevational view of the nozzle of the vaporizing device cartridge system illustrating a septum a in a closed position, in accordance with an embodiment of the present disclosure.

In another embodiment of the present disclosure, the nozzle is constructed with a septum [804] or other similar construction to control the flow of concentrate product from the cartridge. The exemplary nozzle [800] is configured on a cartridge [600, 700] and cooperates thereon the cartridge [600, 700] to provide dose control and dose integrity, respectively. As shown in FIGS. 8B and 8C, the exemplary nozzle [800] includes a tip seal comprised of a nozzle insert [803] and septum [804]. The exemplary septum [804], in a closed position, seals against an insert in the nozzle. Upon turning of the dosing wheel [232], the plunger driver [623] actuates the plunger [621] into the cartridge vessel [605], and thereby causes concentrate product to deform the elastomer septum away from the insert, thus allowing the concentrate to extrude through the tip seal [803] onto a diffuser.

Figure 9:
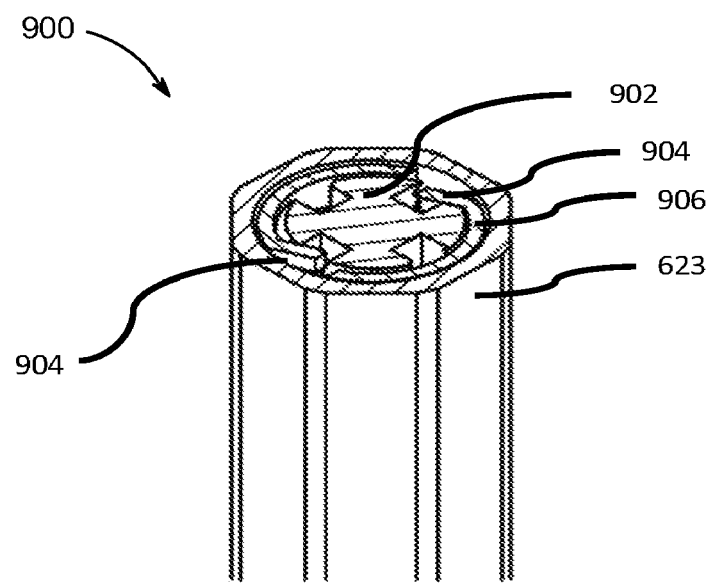
FIG. 9 is a cross-section view of the dose integrity mechanism of the vaporizing device cartridge system, in accordance with an embodiment of the present disclosure.
Figure 10A:
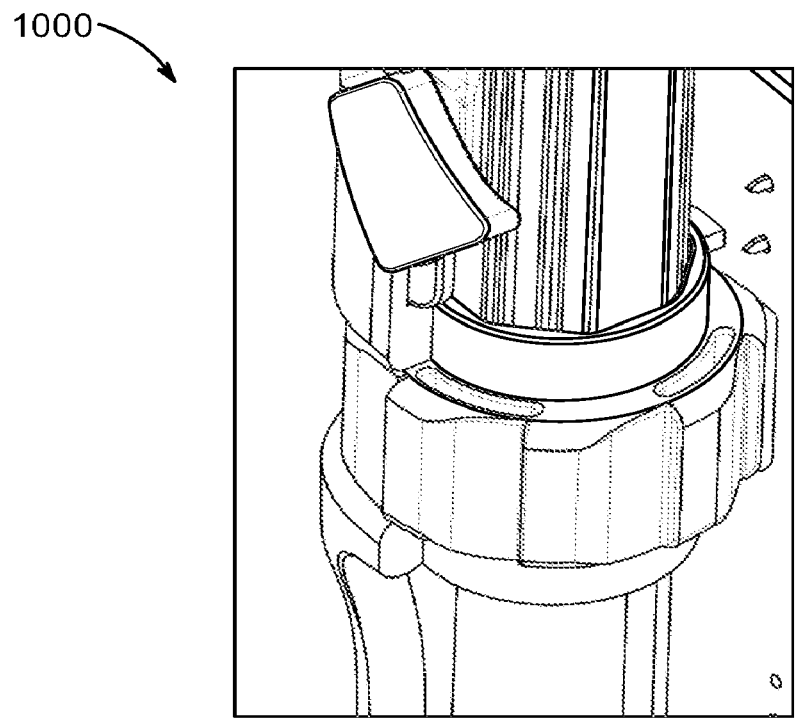
FIGS. 10A and 10B are perspective views of the plunger driver illustrating various components thereon of the vaporizing device cartridge system, in accordance with an embodiment of the present disclosure.
Figure 10B:
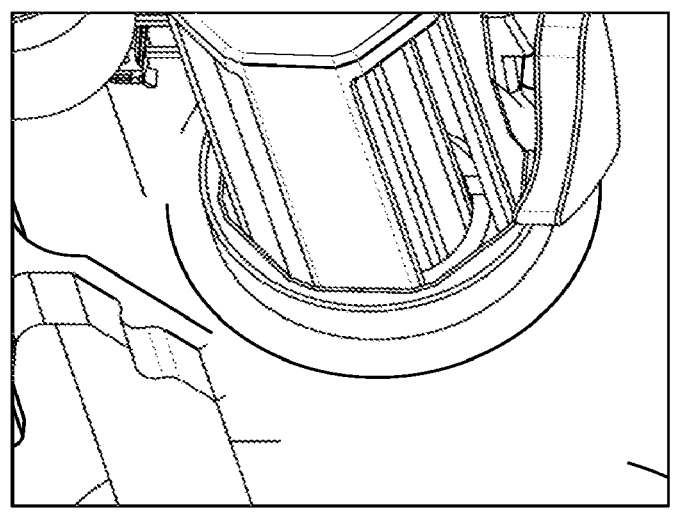
Figure 13:
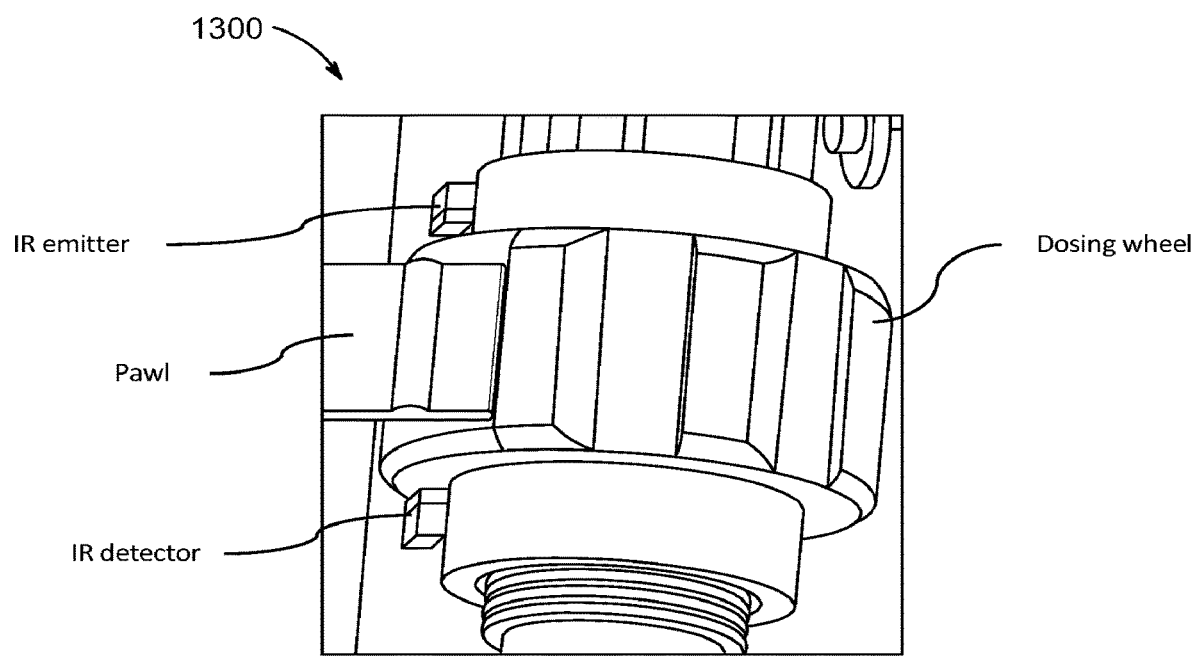
FIG. 13 illustrates various components of the dose completion and verification system of the vaporizing device, in accordance with an embodiment of the present disclosure.

As shown in FIGS. 9, 10B and 13, the dose integrity mechanism [900], according to an embodiment of the present disclosure, includes an anti-unwind feature using a pawls [904] situated in cartridge dosing mechanism assembly [620]. Pawls [904] mate with longitudinal slots [906] in plunger driver [623] and restrict rotational movement of plunger driver [623] in the reverse direction, thereby prohibiting a user from inadvertently unwinding the plunger driver [623]. Exemplary pawls [904] provide additional assurance against confounding of the number of doses delivered via cartridge [600]. In an embodiment, pawl [904] may not be disassembled by a user without disabling the cartridge [600] as pawl [904] is recessed within plunger driver [623] (not shown). In addition, pawl [904] provides anti-back wind of the dosing wheel [232] to mitigate against confounding the dose tracking and management aspects of vaporizer [200].

In an example, plunger driver [623] advances down the threaded body of cartridge lock [625] and applies downward pressure on the plunger [621]. Downward movement of plunger [621] causes concentrate product to extrude out of the nozzle [800]. By way of turning the dosing wheel [232], pawls [904] are spring-tensioned against the cartridge lock [906] and exhibit a "click" sound as pawl [904] comes to rest in slot [906]. The "click" sound provides audible feedback to a user that a desired amount/dose of concentrate product (e.g., 2.5 mg) has been delivered for vaporization.

Figure 11:
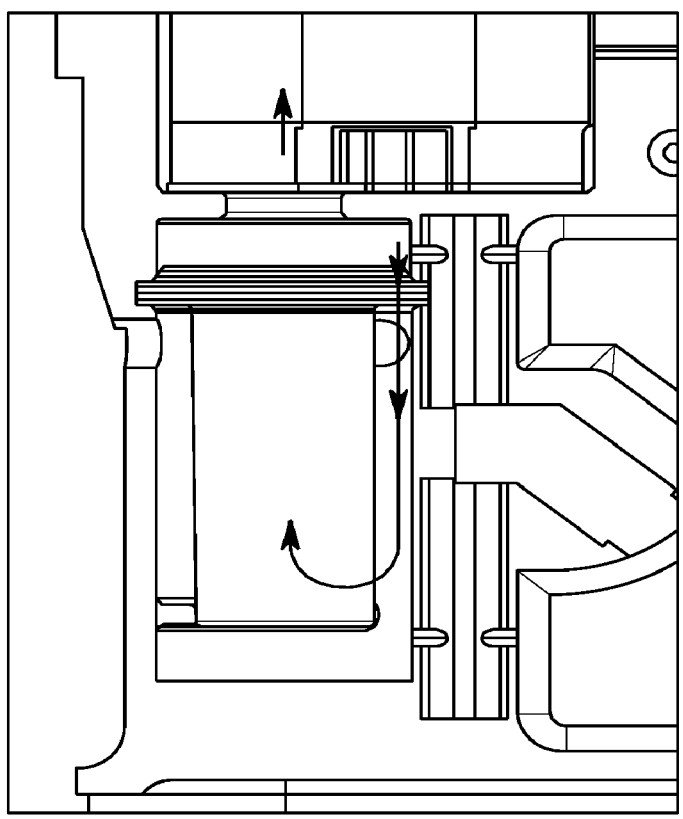
FIG. 11 is a side view of oven system of the vaporizing device, in accordance with an embodiment of the present disclosure.

FIG. 11 illustrates an oven system [1100] in accordance with an embodiment of the present disclosure. The oven system [1100] includes a coil [258] (not shown) located inside a thermally resistant tube [1102], which focuses airflow [1104] on the heating coil [258] for efficient heat transfer from the coil [258] into the negative pressure airflow [1104]. Tube [1102] may be constructed of a ceramic or other material that provides thermal resistance. In an embodiment, ambient air intake [1106] is directed around the outside of tube [1102] into negative pressure airflow [1104] to facilitate enhanced heat transfer from the heating tube [1102].

To improve heating efficiency, the ambient air intake [1106] is directed around the outside of the oven tube to facilitate further heat transfer emanating from the heating tube [1108] and redirecting back into the negative pressure airflow [1104].

Figure 12A:
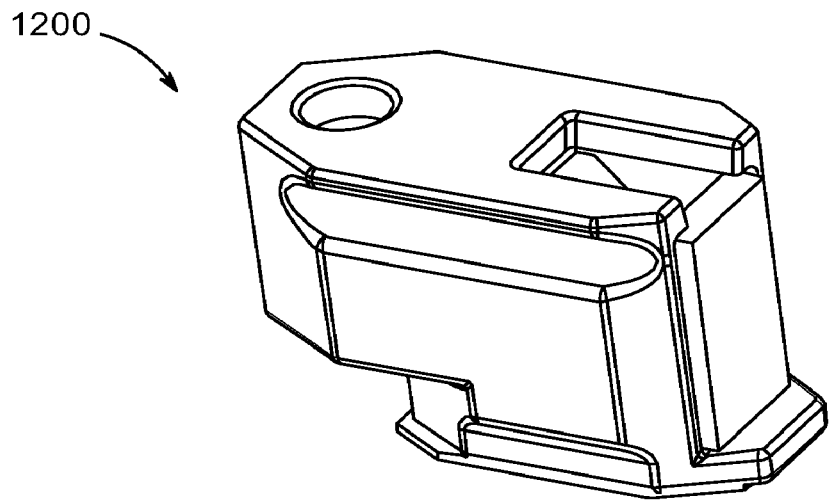
FIGS. 12A and 12B are perspective views of the dose diffuser of the vaporizing device oven system, in accordance with an embodiment of the present disclosure.
Figure 12B:
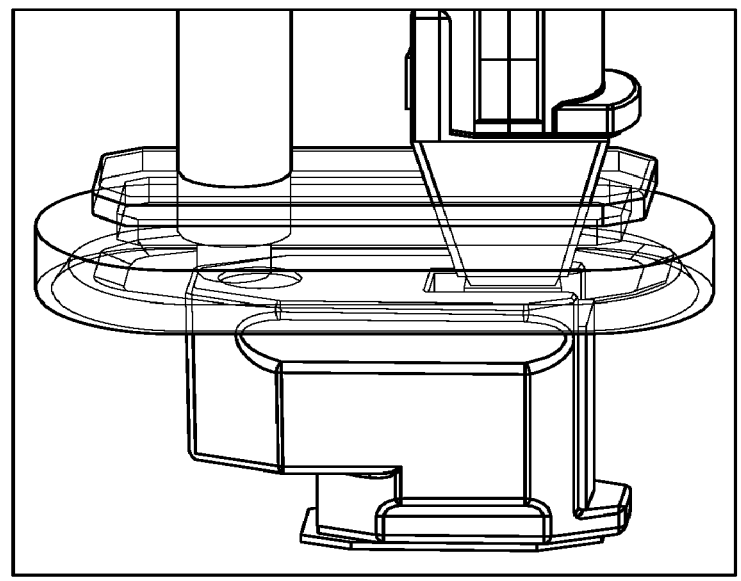
Figure 12C:
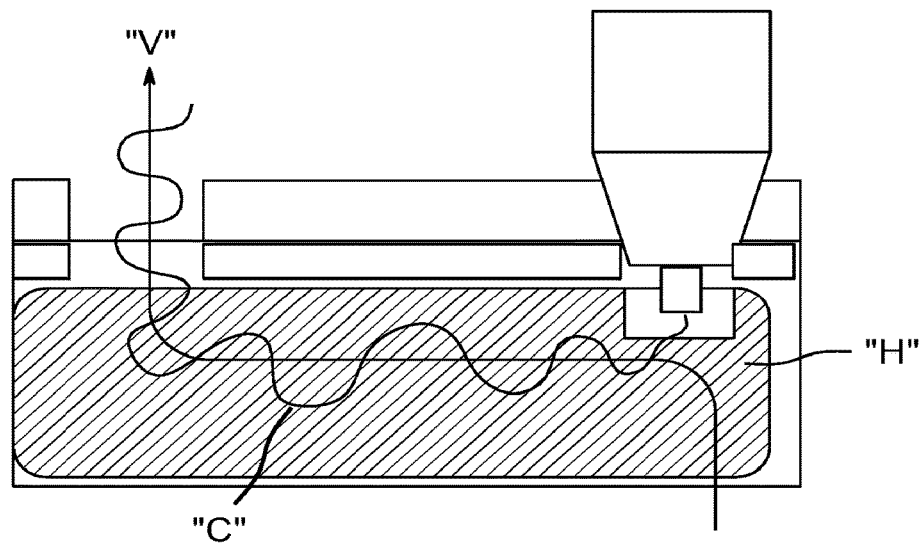
FIG. 12C is a front elevational view of the dose diffuser of the vaporizing device oven system, in accordance with an embodiment of the present disclosure.

The oven system includes a dose diffuser [1200], as shown in FIGS. 12A-12C. The exemplary diffuser [1200] is a two-part component designed to efficiently vaporize concentrate product. The external portion of the diffuser [1200] is made of a thermally resistant ceramic material though other thermally resistant materials may be used. The internal portion of diffuser [1200] is filled with a low density, porous stainless steel matrix or screen [1210]. As an example, the porous stainless steel matrix may be constructed with approximately 60 pores per inch; however, other mesh sizes may be utilized in accordance with an embodiment of the present disclosure.

Porous material [1210] provides a much higher surface/density ratio compared to wire mesh, for greatly improved vaporization efficiency (i.e., more surface area for concentrate to spread, and less substrate to heat). Porous material [1210] also minimizes air resistance compared to wire mesh.

In an aspect of the present disclosure, the exemplary dose diffuser [1210] is configured with three ports. The first port [1211] is directly aligned with the exit port of the heater chamber to allow heat to be drawn up into the porous matrix [1210] during the user's inhalation. The second port [1213] is located proximally opposite the first port [1211] on the top of the diffuser [1200]. Second port [1211] provides means for the nozzle [800] to extend into the interior of the diffuser [1200].

In an embodiment, oven seal [1202] provides an air tight seal between the nozzle [800] and second port [1213]. Seal seat [1202] cooperates with nozzle [800] to eliminate inflow of air into the oven [1100] during negative pressure inhalation by a user. A third port [1215] is directly aligned with conduit [278] (i.e., the vaporized concentrate air path) and provides an air tight seal between the third port [1215] and conduit [278].

By reference to FIG. 13, during operation of the vaporizer of the present disclosure, when the oven cover [266] is closed, the user extrudes concentrate product by indexing the dose wheel [232]. The concentrate is subsequently deposited into the porous matrix [1210]. When the user fires the device and subsequently inhales air through the system, heated air "H" is drawn through the oven [1100], through the internal porous matrix [1210], up the conduit [278] and exits via the mouthpiece [276] into the user [111].

In an exemplary aspect, heated air "H" is drawn through the internal porous matrix thereby heating the porous matrix and the deposited concentrate "C". The concentrate is then flashed through the porous matrix [1210] in the direction of airflow "V". As an example, concentrate oil in the porous matrix [1210] continues to thin and transition to vapor as the vapor transition temperature of the concentrate oil is exceeded. The thermally resistive properties of the vaporizer housing [202] efficiently contains the heat within the porous matrix. The exemplary device [200], as such, provides the ability for micro-dosing of the concentrate oil.

In an exemplary embodiment of the present disclosure, the vaporizer [200] and cartridge system, for example [600] may only provide heated air to vaporize the concentrate when a user applies negative pressure (i.e., inhales) at the mouthpiece. A heating coil [258] is activated when negative air pressure is sensed in the system by using, for example, an inline pressure sensor, a fan/IR reflector sensor, or by monitoring a change in power draw to maintain a set temperature at the coil.

In another exemplary embodiment of the present disclosure, as shown in FIG. 13, the vaporizer device allows a user the ability to deliberately select a desired dose (e.g. micro-dosing) via iterative indexing of the dose wheel [1100]. Each index is captured via pairing an IR emitter/detector arrangement with slots in the dose wheel (i.e., encoder wheel configuration). In one aspect, the vaporizer device notifies a user that they have completed the inhalation of the desired/administered dose. In accordance with this aspect, the device provides a hardware/software feedback loop whereby 1) the user presses and holds the "fire" button, wherein the device draws current from the battery through the heating coil in order to heat the coil to a set temperature, 2) once the set temperature is established and maintained by the PID control system (Note: the change in current draw is small and predictable) the user inhales air through the vaporizer, 3) the incoming air flow cools the heating coil, requiring the device to quickly respond with a ramp up of current in order to maintain the set temperature, and 4) the change in amperage can be detected and thus is used to accurately identify when the user is inhaling from the device.

An IR emitter and detector set are paired on opposite sides of conduit [278] to detect the presence of vapor in the conduit [278]. In an exemplary embodiment, conduit [278] may be a transparent borosilicate glass air path. When vapor is present in conduit [278], it scatters the IR light and results in less being collected by the detector. Therefore, when the user presses and holds the "fire" button and inhales air through the system, the device monitors the presence of vapor traveling up the air path, and it notifies the mobile app that vapor is being inhaled. When no vapor is detected after a set time period while the user is inhaling, the device informs the mobile app via the BLE communication that the dose has been fully inhaled. This completes the feedback loop of knowing how much concentrate product is prepared for delivery (via dose wheel indexing), and when all of the concentrate product has been inhaled.

In yet another exemplary embodiment of the present disclosure, the vaporizer device provides for the retention of the identification code can be achieved by the installation of a smart chip onto the Cartridge that is programmed at time of Cartridge filling. The code can subsequently be used by the App to access unique information corresponding to the identification code, such as product name, distillate fill batch information, laboratory results, product temperature limits, etc. A smart chip, such as an EEPROM is programmable, therefore, the chip can be programmed with information by the device as well during use, such as doses left in the Cartridge. This is helpful not only to the user, but also for protecting against misuse by allowing the device to disable a cartridge should it attempted to be used beyond its programmed volume life.

In another exemplary embodiment of the present disclosure, the vaporizer [200], a removable mouthpiece with integrated diffuser tool is provided, wherein the mouthpiece [276]:
 a) provides cartridge loading access,
 b) is removable and replaceable,
 c) provides an air tight seal at top of conduit,
 d) mates with push button latch on case body to provide intuitive locking and unlocking of mouthpiece to case body,
 e) provides a preload of concentrate product,
 f) serves as a tool to remove the dose diffuser.

Figure 14:
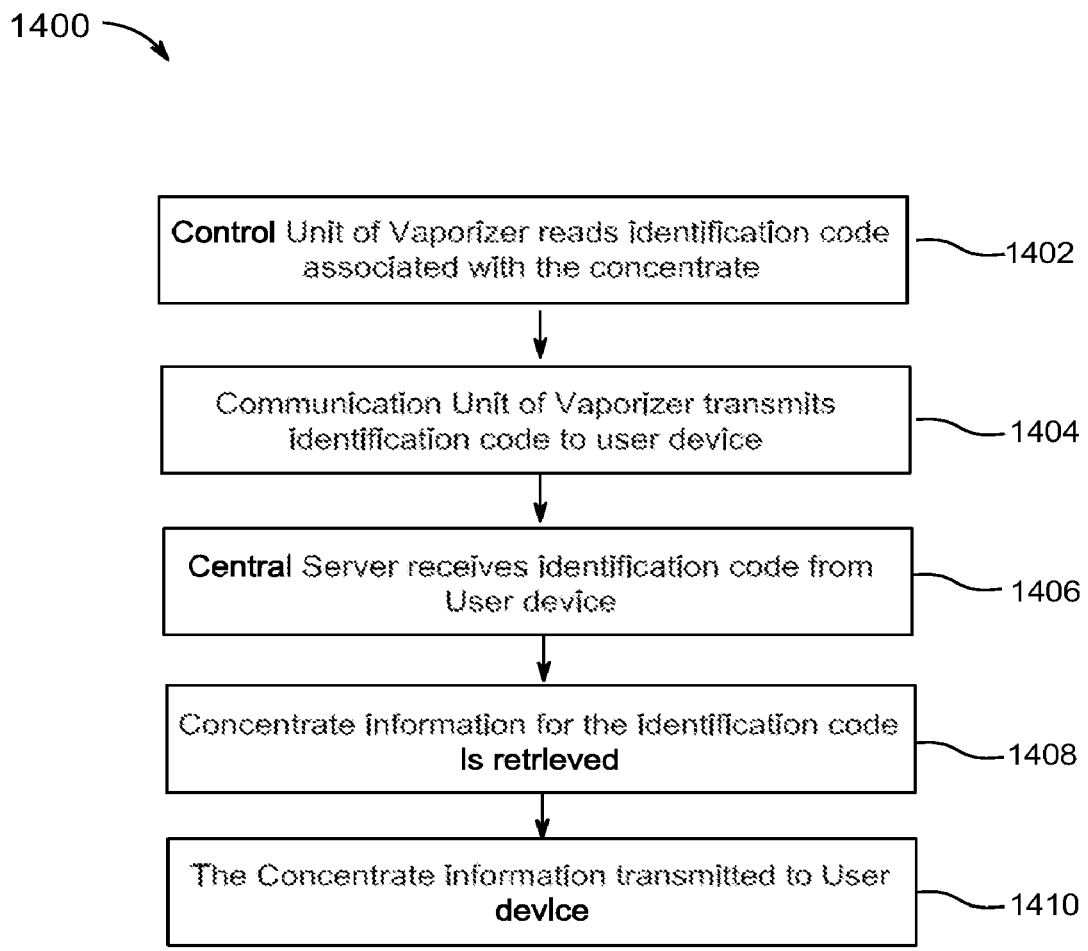
FIG. 14 illustrates a method for managing concentrate usage of a user, in accordance with an embodiment of the present disclosure.

FIG. 14 illustrates a method [1400] for administering the concentrate to the user using the vaporizer [200]. The vaporizer [200] may be configured to monitor and control various aspects of the concentrate usage of the user. The order in which the method [1400] is described is not intended as a limitation, and any number of the described method blocks may be combined in any order to implement the method, or an alternative method. Additionally, individual blocks may be deleted from the method without departing from the spirit and scope of the present disclosure.

At step [1402], a control unit of a vaporizer reads an identification code associated with a concentrate. At step [1404], a communication unit of the vaporizer may transmit the identification code to a user device. At step [1406], a central server may receive the identification code from the user device, wherein the central server comprises a database storing a plurality of identification codes against a plurality of concentrate information. At step [1308], concentrate information corresponding the received identification code is retrieved from the database. At step [1410], the retrieved concentrate information is transmitted to the user device for displaying to a user.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of" Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

The terms "determine", "calculate" and "compute," and variations thereof, as used herein, are used interchangeably and include any type of methodology, process, mathematical operation or technique.

The foregoing discussion of the present disclosure has been presented for purposes of illustration and description. The foregoing is not intended to limit the present disclosure to the form or forms disclosed herein. In the foregoing Detailed Description for example, various features of the present disclosure are grouped together in one or more embodiments, configurations, or aspects for the purpose of streamlining the disclosure. The features of the embodiments, configurations, or aspects of the present disclosure may be combined in alternate embodiments, configurations, or aspects other than those discussed above. This method of disclosure is not to be interpreted as reflecting an intention that the present disclosure requires more features than are expressly recited in each claim. Rather, as the following claims reflect, the claimed features lie in less than all features of a single foregoing disclosed embodiment, configuration, or aspect. Thus, the following claims are hereby incorporated into this Detailed Description, with each claim standing on its own as a separate embodiment of the present disclosure.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

LIST OF ELEMENTS

- 100 system
- 102 vaporizer
- 104 cartridge
- 106 control unit
- 108 communication unit
- 110 user device
- 111 user
- 112 central server
- 114 database
- 116 user profile data
- 117 user(s)
- 200 vaporizer
- 202 housing
- 204 first half
- 206 second half
- 208 groove
- 210 cartridge
- 211 storage vessel
- 212 plunger driver
- 213 pawl
- 214 plunger
- 216 memory module
- 218 nozzle
- 220 control unit
- 224 communication unit
- 226 power source
- 232 dosing wheel
- 249 cut-out
- 250 oven
- 252 oven casing
- 256 vaporization chamber
- 258 coil
- 260 dose diffuser
- 266 oven cover
- 272 vent
- 276 mouthpiece
- 278 conduit
- 280 power button
- 282 fire button
- 600 cartridge
- 601 nozzle
- 602 smart chip
- 603 nozzle insert
- 605 cartridge body, storage vessel
- 610 tip seal assembly
- 615 nozzle cap
- 620 dosing mechanism assembly
- 621 plunger
- 623 plunger driver
- 625 cartridge lock
- 700 cartridge, non-liquid
- 701 driver
- 703 auger
- 706 nut
- 707 cartridge body
- 710 nozzle
- 712 smart chip
- 800 nozzle
- 802 groove
- 803 tip seal
- 804 septum
- 805 nozzle insert
- 807 nozzle port
- 809 cartridge body
- 900 dose integrity mechanism
- 902 plunger
- 904 pawls
- 906 cartridge lock
- 910 plunger driver
- 1000 plunger driver
- 1100 oven system
- 1200 diffuser
- 1210 porous matrix 1400 method
1402 step
1404 step
1406 step
1408 step
1410 step

What is claimed is:

1. A system for managing concentrate usage, the system comprising:
a vaporizer comprising:
a housing comprising;
a cartridge configured to store a concentrate, wherein the cartridge comprises a concentrate storage vessel, a nozzle, at one end, a smart chip configured on the nozzle to track and record concentrate dose amount in a concentrate storage vessel, said smart chip comprising an identification code associated with the concentrate, and a dosing mechanism at other end, the dosing mechanism comprises a plunger driver, a pawl, and a plunger, and wherein upon rotation of a dosing wheel by a user, the plunger driver drives the plunger within the cartridge to release a predefined quantity of the concentrate through the nozzle;
a control unit configured to read the identification code from the smart chip and control operation of an oven;
a vapor detection system comprising IR emitter and detector configured to detect concentrate vapor in a conduit upon a user inhalation of vaporized concentrate; and
a communication unit coupled to the control unit, wherein the communication unit transmits the identification code to a user device;
a central server comprising a database storing a plurality of identification codes against a plurality of concentrate information, wherein the central server is configured to:
receive the identification code from the user device;
retrieve concentrate information corresponding the received identification code from the database; and
transmit the retrieved concentrate information to the user device.

2. The system of claim 1, wherein the oven comprises a coil placed within a thermally resistant tube, an airflow channel in communication with ambient air and inhalation negative pressure airflow, and a dose diffuser containing a porous material matrix.

3. The system of claim 2, wherein the control unit is configured to heat the coil of the oven based on at least one of a fire button, an in-line pressure sensor, a fan/IR reflector sensor, and the identification code associated with the concentrate.

4. The system of claim 3, wherein the control unit heats the coil to vaporize the predefined quantity of the concentrate released through the nozzle on the porous material matrix or screen of the dose diffuser.

5. The system of claim 1, wherein the user device is configured to:
receive at least one user input related to a vaping session of the user; and
transmit at least one instruction to the vaporizer based on the received user input for triggering the vaping session.

6. The system of claim 5, wherein the user device is configured to:

generate a session data associated with the vaping session; and
transmit the session data to the central server.

7. The system of claim 6, wherein the central server is configured to:
receive the session data from the user device; and
update a user profile based on the session data, wherein the user profile comprises data associated with one or more vaping sessions of the user.

8. The system of claim 5, wherein the user device is configured to:
display a survey related to the vaping session of the user;
receive a user feedback on the survey; and
transmit the user feedback to the central server.

9. The system of claim 1, wherein the communication unit of the vaporizing device comprises a Bluetooth Low Energy (BTLE) and/or WiFi module.

10. The system of claim 1, wherein the user device displays a dosage information based on at least one of the retrieved concentrate information, the user profile, user's medical history, and the vaping session.

11. A method for managing concentrate usage of a user, the method comprising:
reading, by a control unit of a vaporizer, an identification code associated with a concentrate;
transmitting, by a communication unit of the vaporizer, the identification code to a user device and/or system network;
receiving, by a central server, the identification code from the user device, wherein the central server comprises a database storing a plurality of identification codes against a plurality of concentrate information;
retrieving concentrate information corresponding to the received identification code from the database; and
transmitting the retrieved concentrate information to the user device for displaying to a user;
wherein the vaporizer comprises:
a housing comprising;
a cartridge configured to store the concentrate, wherein the cartridge comprises a concentrate storage vessel, a nozzle, at one end, a smart chip configured on the nozzle to track and record concentrate dose amount in a concentrate storage vessel, said smart chip comprising an identification code associated with the concentrate and a dosing mechanism at other end;
an oven comprising a coil placed within a thermally resistant tube, an airflow channel in communication with ambient air and inhalation negative pressure airflow, and a dose diffuser containing a porous material matrix; and
the control unit configured to read the identification code from the smart chip and control operation of an oven, wherein the oven is adjacent to the nozzle of the cartridge; and
the communication unit coupled to the control unit, wherein the communication unit transmits the identification code to the user device.

12. The method of claim 11, further comprising:
receiving at least one user input related to a vaping session; and
transmitting at least one instruction to the vaporizer based on the received user input for triggering the vaping session.

13. The method of claim 12, further comprising:
generating a session data associated with the vaping session; and transmitting the session data to the central server for updating a user profile, wherein the user profile comprises a data associated with one or more vaping sessions of the user.

14. The method of claim 12, further comprising:
displaying to the user a survey related to the vaping session;
receiving a user feedback on the survey; and
transmitting the user feedback to the central server.

15. The method of claim 11, further comprising displaying, on the user device, a dosage information based on at least one of the retrieved concentrate information, the user profile, user's medical history, and a vaping session.

16. A vaporizer comprising:
a housing comprising;
   a cartridge configured to store a concentrate, wherein the cartridge comprises a concentrate storage vessel, a nozzle, at one end, a smart chip with an identification code associated with the concentrate and a dosing mechanism at other end, and wherein the dosing mechanism comprises, a plunger driver, a pawl, and a plunger;
   a dosing wheel to actuate the dosing mechanism, wherein the dosing wheel is rotatably engaged to the plunger driver;
   an oven comprising a coil placed within a thermally resistant tube, an airflow channel in communication with ambient air and inhalation negative pressure airflow, and a dose diffuser containing a porous material matrix; and
   a control unit configured to heat the coil of the oven based on at least one of a fire button, an in-line pressure sensor, a fan/IR reflector sensor, and the identification code associated with the concentrate;
   a vapor detection system comprising IR emitter and detector configured to detect concentrate vapor in a conduit upon a user inhalation of vaporized concentrate;
   a smart chip configured to track and record concentrate dose amount in a concentrate storage vessel; and
   wherein upon creation of a negative pressure by a user through inhalation via a mouthpiece, the control unit heats the coil, the coil being configured to heat the airflow created by the negative pressure and wherein heated airflow vaporizes an extruded concentrate, and wherein the extruded concentrate is dispensed through the nozzle on the porous material matrix of the dose diffuser after the dosing wheel is rotated by the user and the plunger driver drives the plunger within the cartridge to release a predefined quantity of the concentrate.

17. The vaporizer of claim 16, wherein the mouthpiece is removable to slidably receive the cartridge within the housing.

18. The vaporizer of claim 16, wherein the identification code associated with the concentrate is stored in a memory module consisting at least one of near field communication (NFC) means, QR code, barcode, smart chip, and radio frequency identification (RFID) tag, and wherein the memory module is communicably coupled to the control unit.

19. The vaporizer of claim 16, wherein the dosing mechanism is an auger delivery mechanism.

20. The vaporizer of claim 16, wherein the dosing wheel is a hollow cylinder that circumscribes the plunger driver such that the rotation of the dosing wheel results in a rotation of the plunger driver.

21. The vaporizer of claim 20, wherein the plunger driver is mechanically engaged with the plunger and the pawl, the plunger being driven laterally downwards upon the rotation of the plunger driver due to the rotation of the dosing wheel by the user.

22. The vaporizer of claim 21, wherein the pawl allows the unidirectional rotation of the dosing wheel in either clockwise or anti-clockwise direction.

23. The vaporizer of claim 20, wherein the dosing wheel clicks upon rotation to a predefined degree, and wherein one click of the dosing wheel releases the predefined amount of the concentrate through the nozzle.

24. The vaporizer of claim 16, further comprising a communication unit configured to transmit the identification code to a user device, wherein the user device is configured to display information associated with the concentrate based on the identification code.

25. The vaporizer of claim 24, wherein the control unit is configured to receive instructions from the user device via the communication unit to activate heating of the coil.

26. The vaporizer of claim 24, wherein the user device displays a dosage information based on at least one of the identification code, user's identity, user's medical history, and previous dosage.

27. The vaporizer of claim 16, further comprising a power source in communication with the control unit, wherein the power source is configured to supply electrical energy to the coil.

28. The vaporizer of claim 27, further comprising a power button located on the housing and in communication with the control unit, wherein the power button upon being pressed by the user allows supply of electrical energy from the power source to the coil.

29. The vaporizer of claim 16, further comprising a conduit proximal to the dose diffuser, wherein the conduit connects with the mouthpiece to allow travel of the vaporized concentrate upon user inhalation.

30. The vaporizer of claim 29, further comprising a filter located downstream of the conduit for filtering the vaporized concentrate.

31. The vaporizer of claim 16, wherein the dosing wheel, plunger-driver, and plunger rotates unidirectionally.

32. The vaporizer of claim 16, further comprising an infrared emitter and detector pair, wherein the infrared emitter and detector pair records indexing of the dosing wheel.

33. The vaporizer of claim 16, further comprising a tip seal configured to prevent breach of the cartridge storage vessel.

34. A cartridge configured to store a concentrate comprising:
a concentrate storage vessel;
a nozzle, at one end;
a smart chip configured on the cartridge to track and record concentrate dose amount in a concentrate storage vessel, said smart chip comprising an identification code associated with the concentrate, wherein the smart chip is communicatively coupled with a control unit configured to read the identification code from the smart chip, said control unit configured to control operation of a vaporizer; and
a dosing mechanism at other end, wherein the dosing mechanism comprises a plunger driver, a pawl, and a plunger.

35. The cartridge of claim 34, wherein the dosing mechanism is communicatively coupled to a dosing wheel to actuate the dosing mechanism, wherein the dosing wheel is rotatably engaged to the plunger driver.

36. The cartridge of claim 34, further comprising a tip seal, wherein the tip seal comprises a septum.

37. The cartridge of claim 34, wherein the dosing wheel, plunger-driver, and plunger cooperatively rotates unidirectionally.

38. The cartridge of claim 34, wherein the pawl is concealed by the assembly of the plunger, plunger driver, and a cartridge lock to prevent dismantling, concentrate refilling, or other breach of the concentrate storage vessel.

39. The cartridge of claim 34, wherein the smart chip comprises means for tracking dosage of originally manufactured concentrate from the cartridge, and wherein the smart chip further comprising means for preventing refilling of the concentrate storage vessel and/or reprogramming the smart chip.

* * * * *